(12) United States Patent
Sawada et al.

(10) Patent No.: US 7,880,368 B2
(45) Date of Patent: Feb. 1, 2011

(54) ULTRASONIC TRANSDUCER, ULTRASONIC TRANSDUCER ARRAY AND ULTRASOUND ENDOSCOPE APPARATUS

(75) Inventors: Yukihiko Sawada, Yoshikawa (JP); Katsuhiro Wakabayashi, Tokyo (JP); Akiko Mizunuma, Tokyo (JP); Takuya Imahashi, Kawasaki (JP); Sunao Sato, Tokyo (JP)

(73) Assignee: Olympus Corporation, Tokyo (JP)

( * ) Notice: Subject to any disclaimer, the term of this patent is extended or adjusted under 35 U.S.C. 154(b) by 980 days.

(21) Appl. No.: 11/663,382

(22) PCT Filed: Sep. 6, 2005

(86) PCT No.: PCT/JP2005/016341

§ 371 (c)(1),
(2), (4) Date: Mar. 21, 2007

(87) PCT Pub. No.: WO2006/033232

PCT Pub. Date: Mar. 30, 2006

(65) Prior Publication Data

US 2007/0293762 A1    Dec. 20, 2007

(30) Foreign Application Priority Data

Sep. 21, 2004  (JP) ............................. 2004-273074
Sep. 21, 2004  (JP) ............................. 2004-273075
Sep. 29, 2004  (JP) ............................. 2004-282956

(51) Int. Cl.
*H01L 41/08* (2006.01)

(52) U.S. Cl. .................. 310/334; 310/322; 310/327; 310/369

(58) Field of Classification Search ............... 310/322, 310/327, 334, 369
See application file for complete search history.

(56) References Cited

U.S. PATENT DOCUMENTS

| 4,220,887 A | * | 9/1980 | Kompanek .................. 310/334 |
| 4,604,542 A | * | 8/1986 | Thompson .................. 310/334 |
| 4,651,044 A | * | 3/1987 | Kompanek ............. 310/323.17 |
| 4,774,427 A | * | 9/1988 | Plambeck .................... 310/321 |
| 5,103,130 A | * | 4/1992 | Rolt et al. .................... 310/337 |
| 5,256,920 A | * | 10/1993 | Porzio ......................... 310/13 |

(Continued)

FOREIGN PATENT DOCUMENTS

EP    0458146 A2  *  11/1991

(Continued)

OTHER PUBLICATIONS

Japanese Office Action dated Apr. 6, 2010 with translation.

(Continued)

*Primary Examiner*—Thomas M Dougherty
(74) *Attorney, Agent, or Firm*—Scully, Scott, Murphy & Presser, P.C.

(57) ABSTRACT

An ultrasonic transducer arraying at even intervals ultrasonic transducers for transmitting and receiving ultrasonic waves and layering a plurality of acoustic matching layers on them, comprising an transducer shape forming member made of a fiber-reinforced thermosetting PPE for filling a gap formed on the side face of the ultrasonic transducer with the same material as that of the acoustic matching layer, mixing a colorant in a division member adjacent to a predefined ultrasonic transducer from among a plurality of ultrasonic transducers, and arraying the plurality thereof.

6 Claims, 53 Drawing Sheets

U.S. PATENT DOCUMENTS

| | | | |
|---|---|---|---|
| 5,648,942 A | 7/1997 | Kunkel, III | |
| 6,069,845 A * | 5/2000 | Ambs | 367/165 |
| 6,104,126 A | 8/2000 | Gilmore | |
| 7,093,343 B2 * | 8/2006 | Osborn | 29/594 |
| 7,205,707 B2 * | 4/2007 | Masters et al. | 310/367 |
| 7,221,077 B2 * | 5/2007 | Sawada | 310/369 |
| 7,466,066 B2 * | 12/2008 | Porzio et al. | 310/334 |
| 7,670,335 B2 * | 3/2010 | Keidar | 606/27 |
| 7,719,926 B2 * | 5/2010 | Brogan et al. | 367/159 |
| 2004/0100163 A1 | 5/2004 | Baumgartner et al. | |

FOREIGN PATENT DOCUMENTS

| | | |
|---|---|---|
| EP | 1 384 525 A2 | 1/2004 |
| JP | 63-14623 | 3/1988 |
| JP | 02-002300 | 1/1990 |
| JP | 2-195481 | 8/1990 |
| JP | 02-271839 | 11/1990 |
| JP | 04-152800 | 5/1992 |
| JP | 2502685 | 3/1996 |
| JP | 8-89505 | 4/1996 |
| JP | 9-320713 | 12/1997 |
| JP | 10-285695 | 10/1998 |
| JP | 11-501245 | 2/1999 |
| JP | 11-56852 | 3/1999 |
| JP | 11-205899 | 7/1999 |
| JP | 2002-224104 | 8/2002 |
| JP | 2003-61954 | 3/2003 |
| WO | WO 97/23865 | 7/1997 |

OTHER PUBLICATIONS

EPC Communication dated Jul. 13, 2010.

* cited by examiner

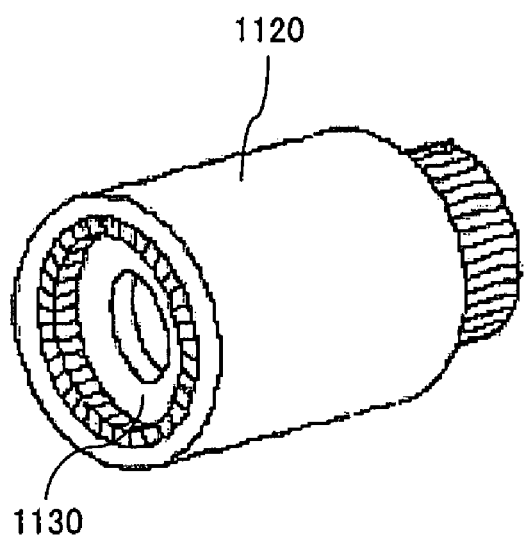
F I G. 4

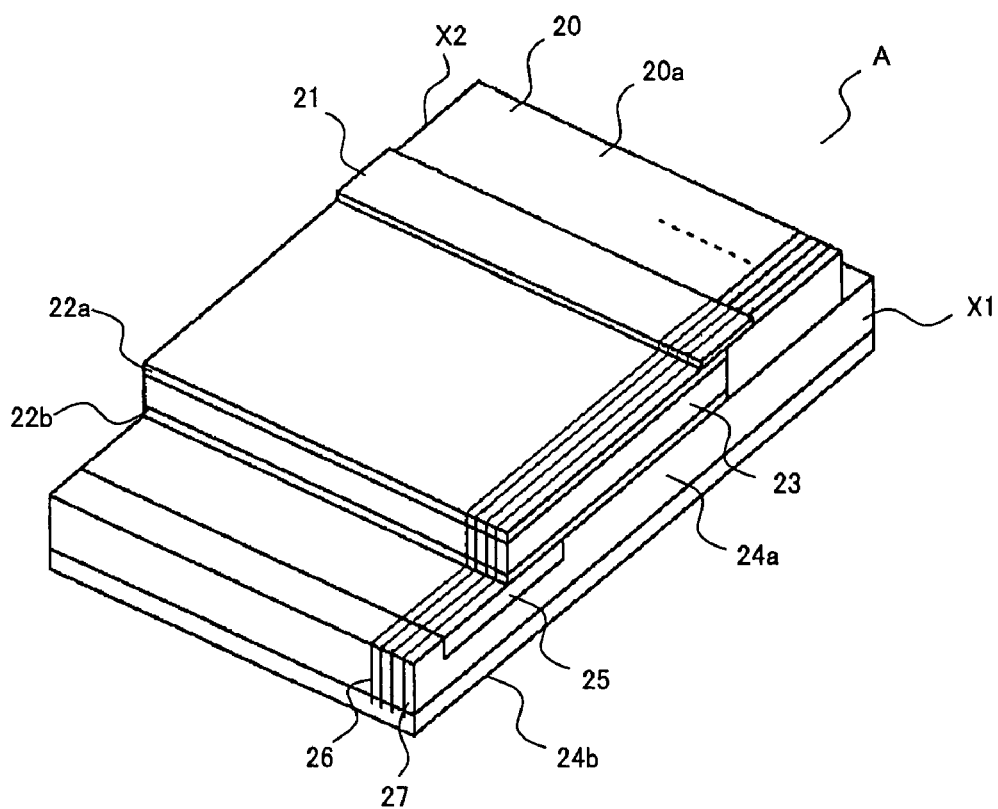
F I G. 8

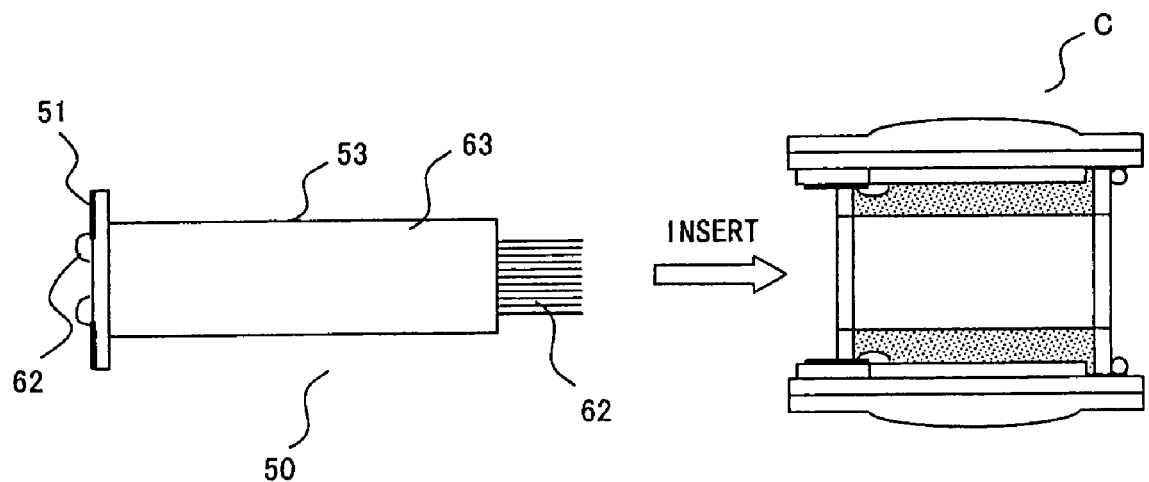
F I G. 16 A
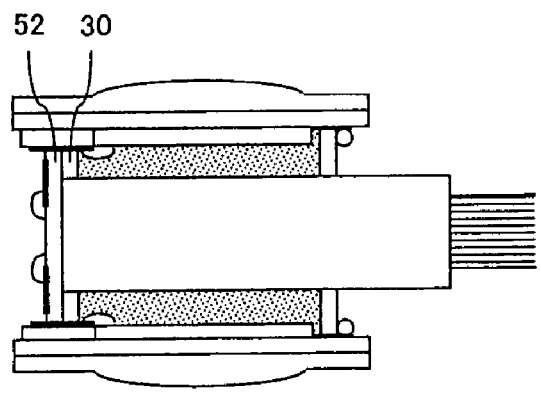
F I G. 16 B

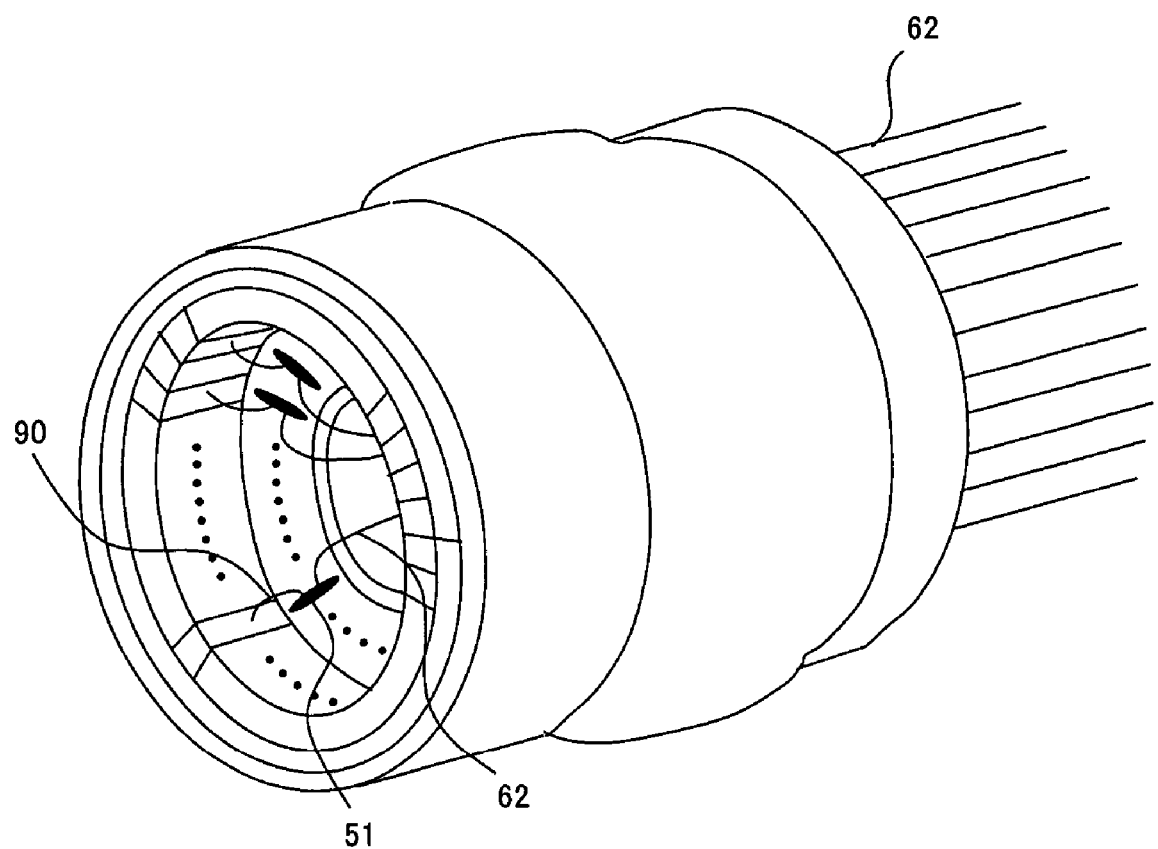
F I G. 17

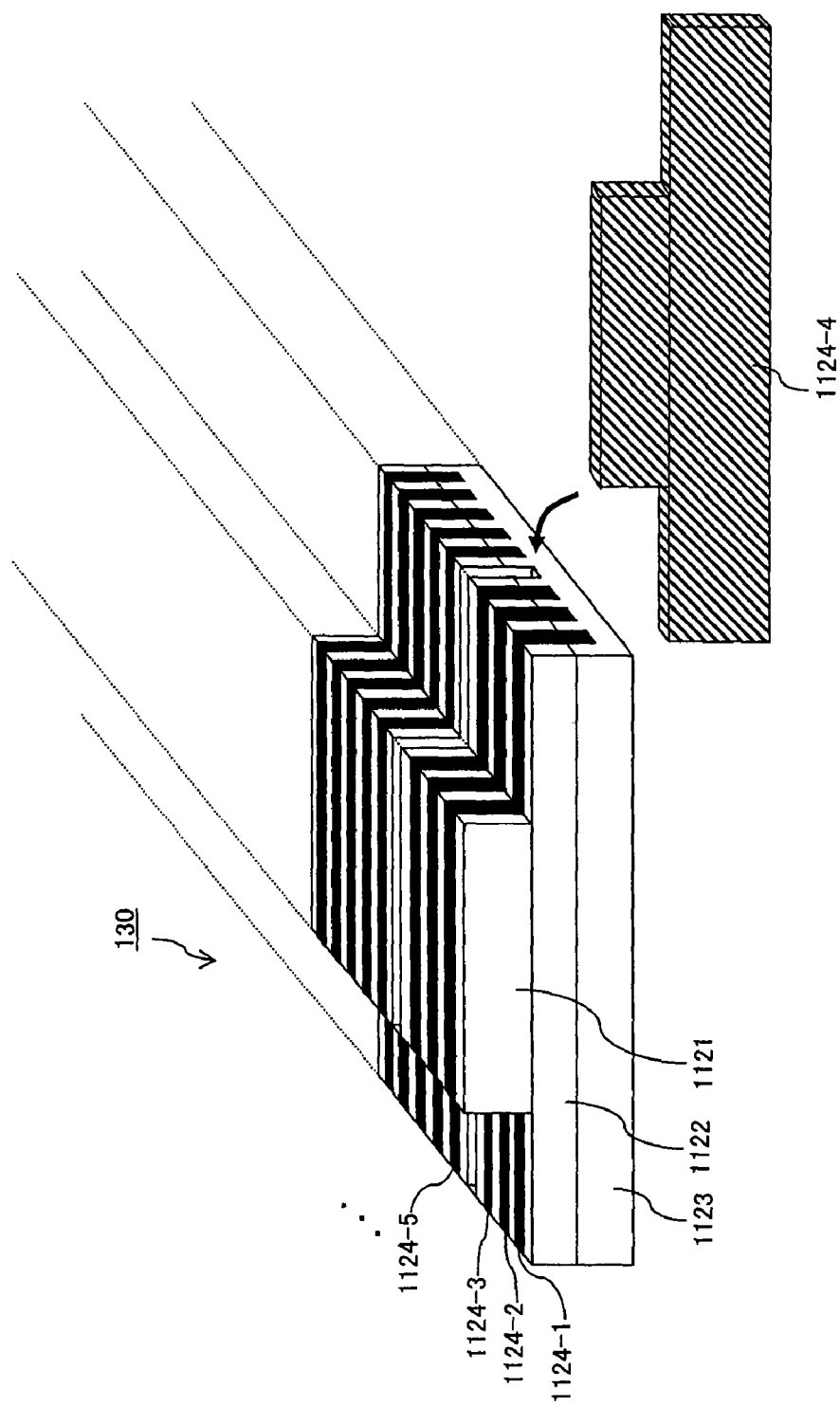
F I G. 2 1

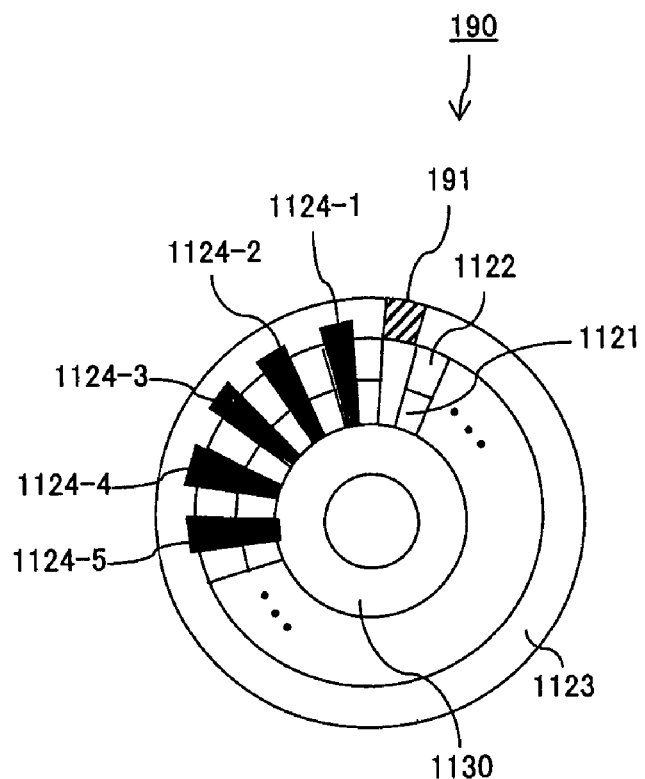
F I G. 27

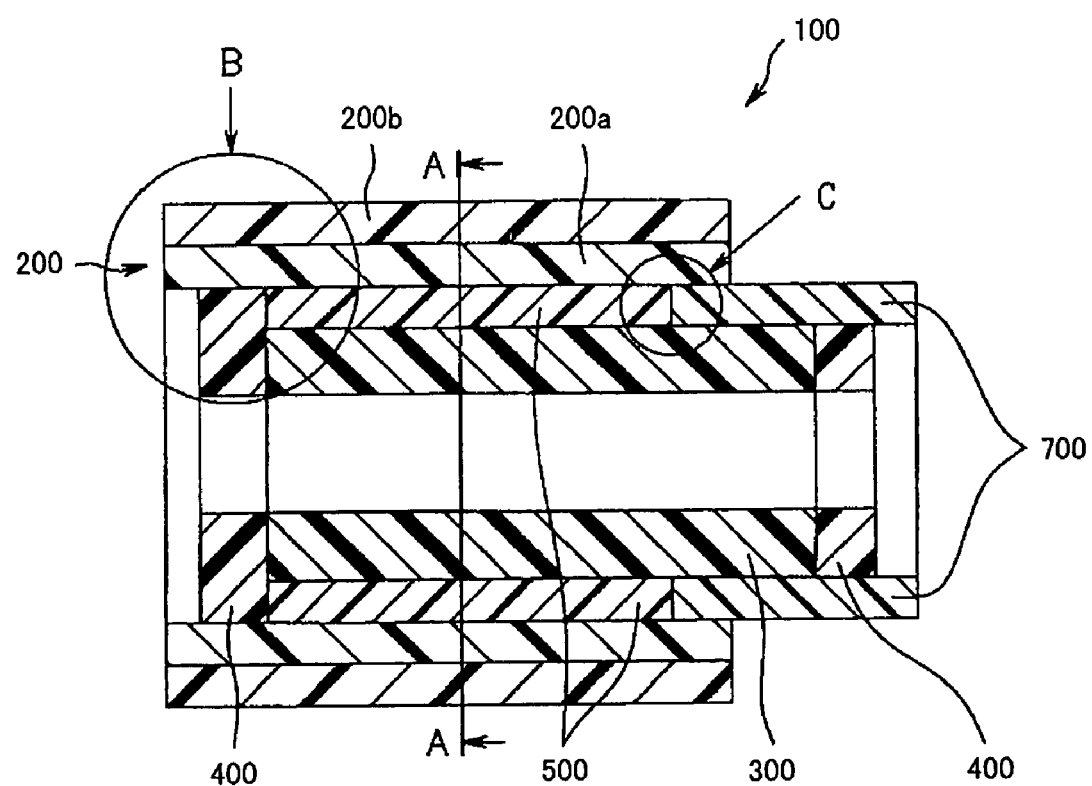
F I G. 29

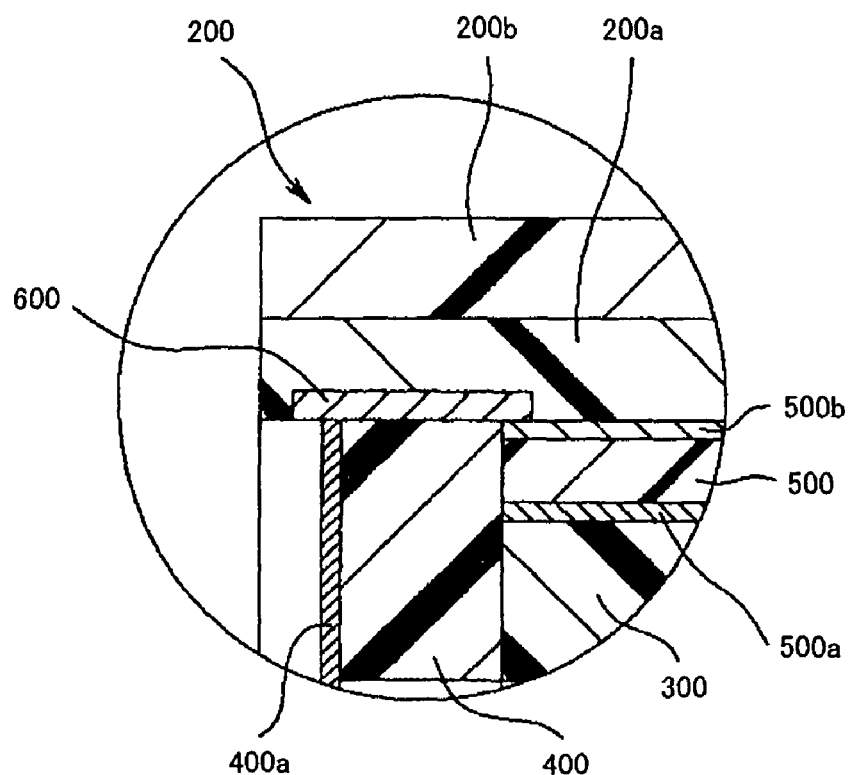
F I G. 33

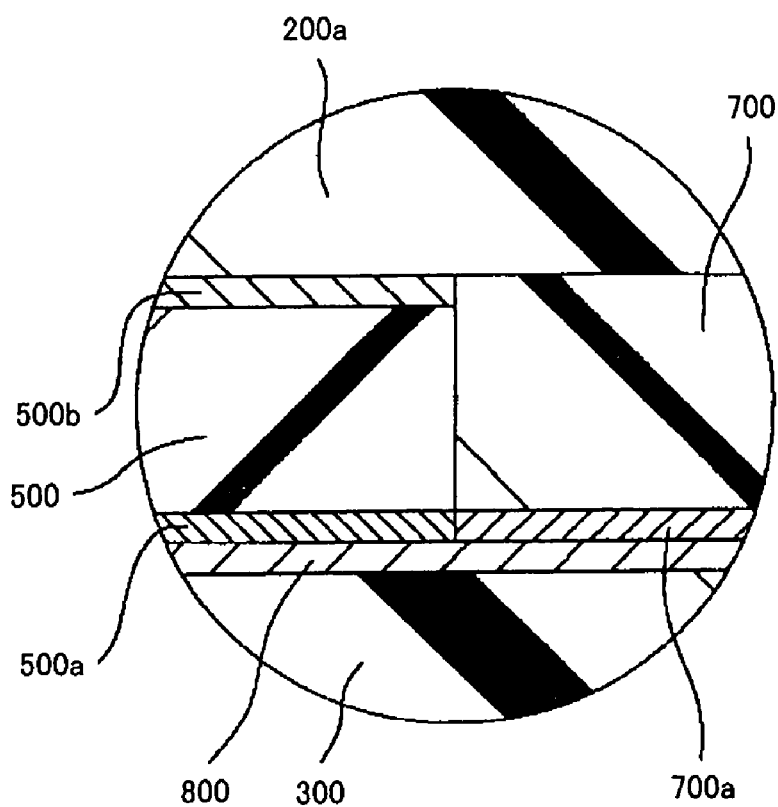
F I G. 3 4

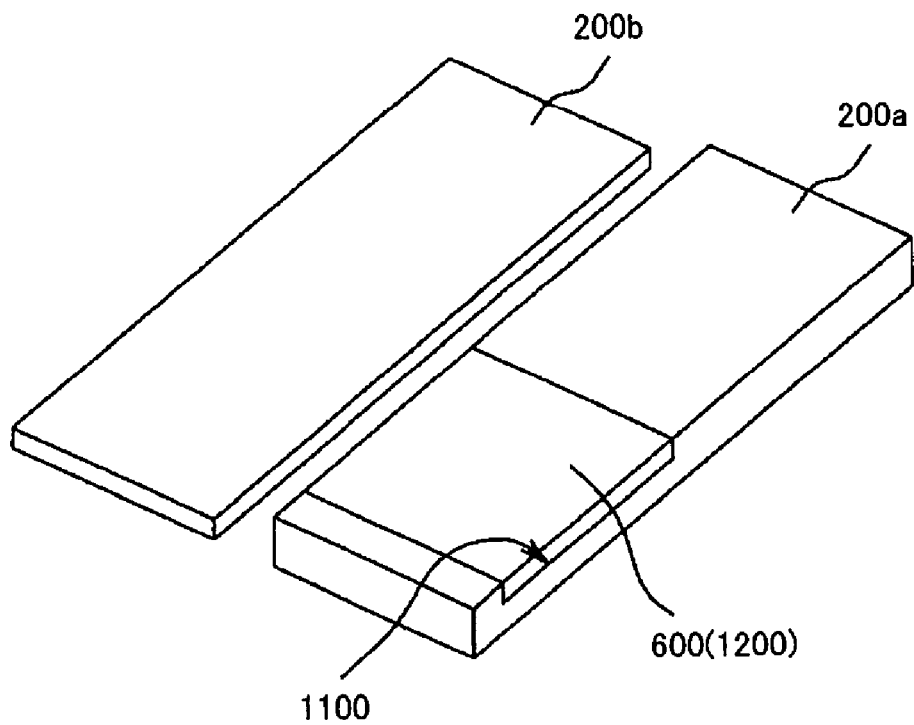
F I G. 3 5

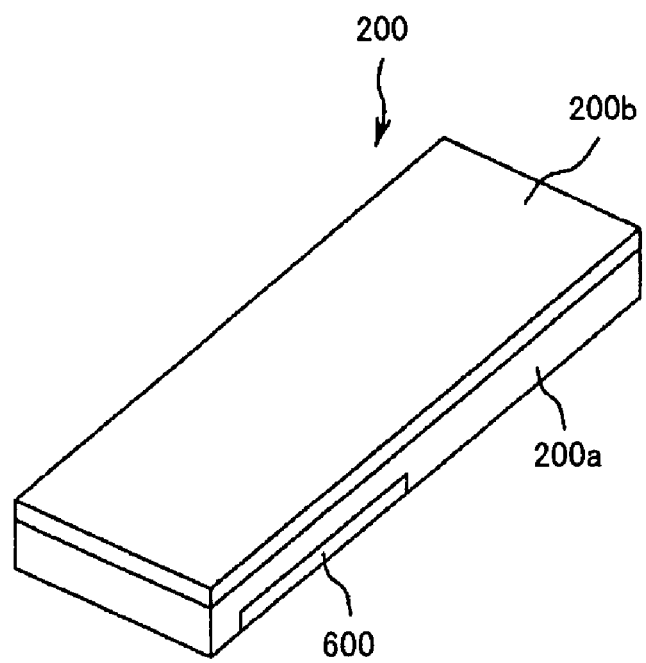
F I G. 36

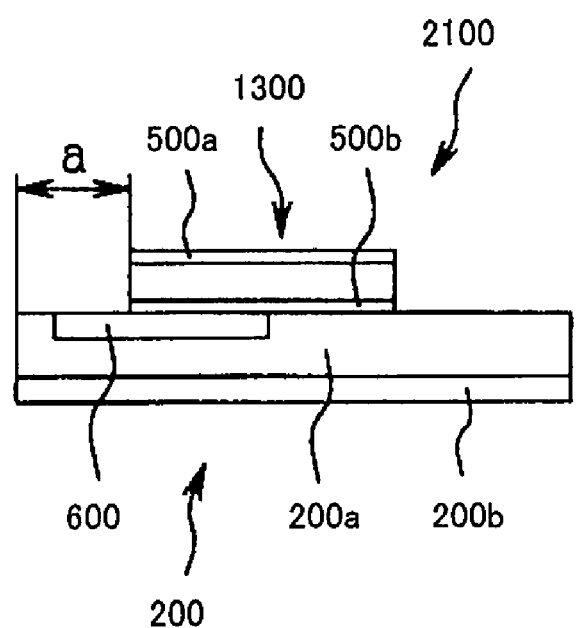
F I G. 3 8

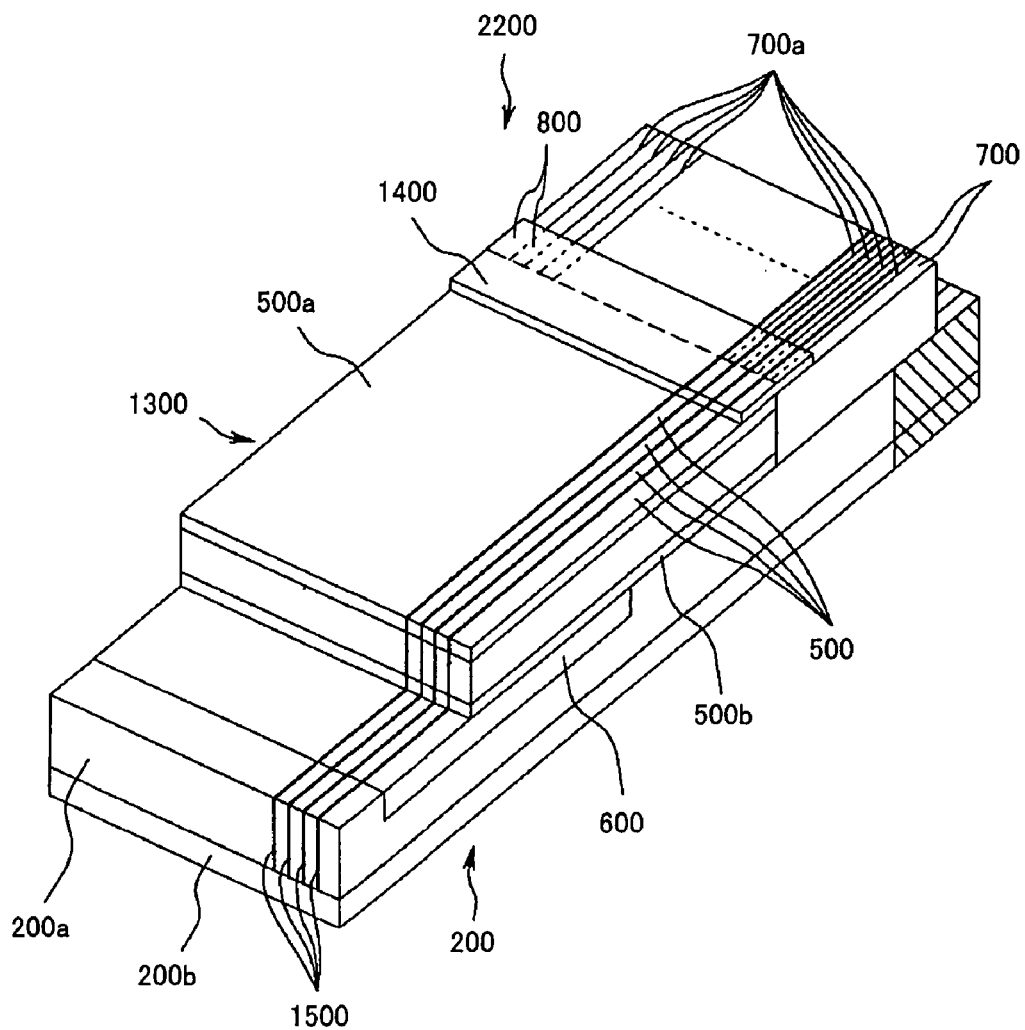
F I G. 4 2

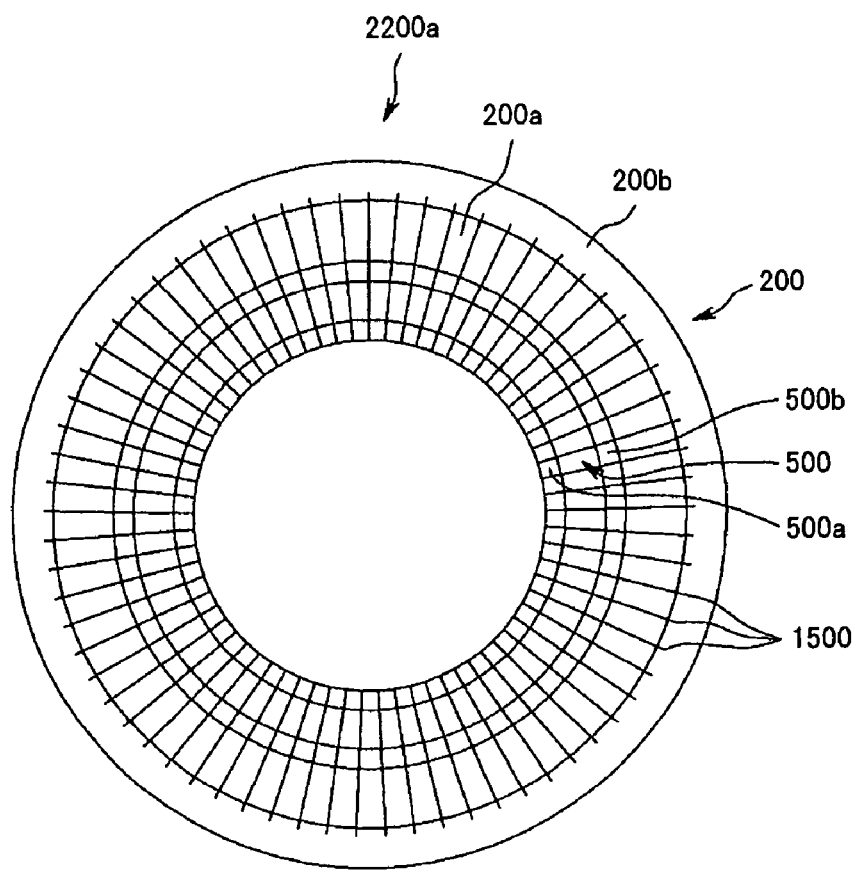
F I G. 44

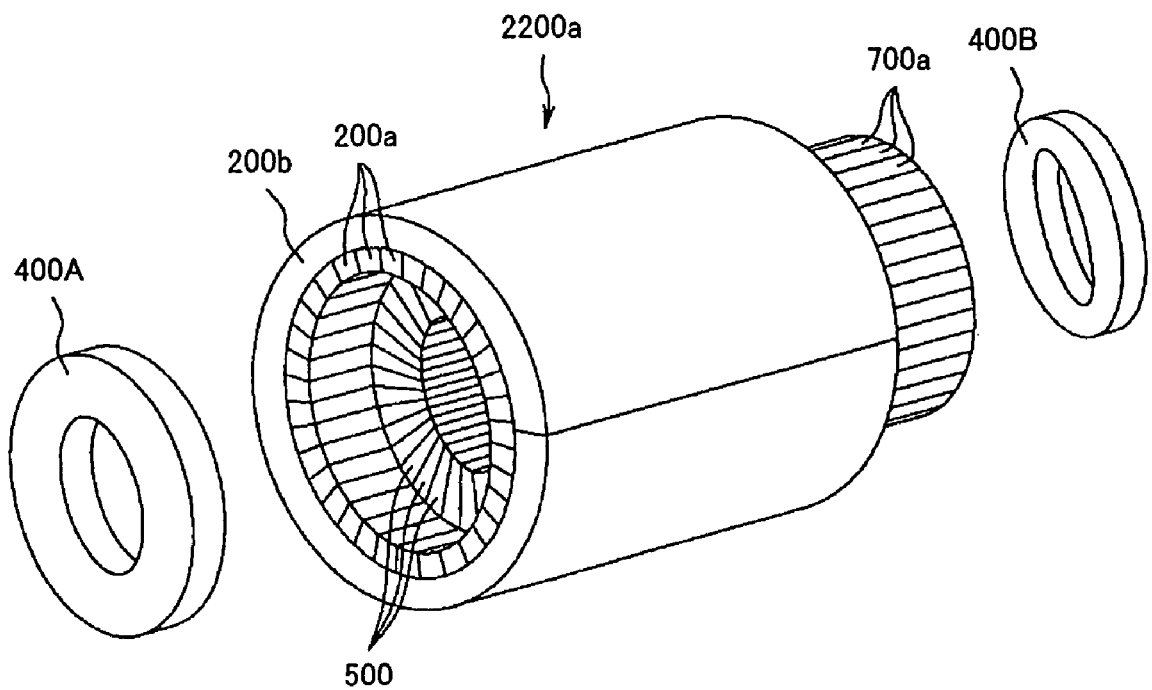
F I G. 45

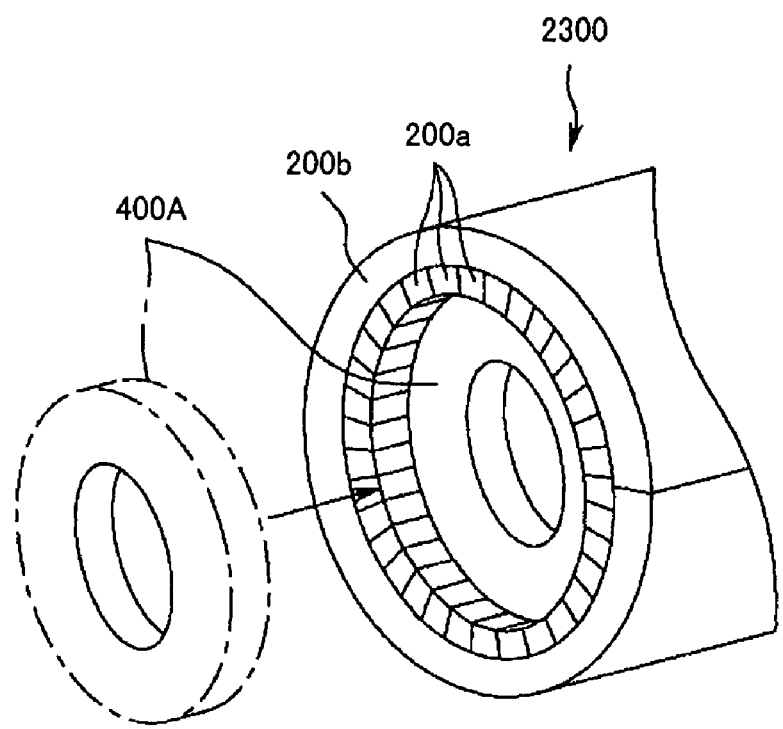
F I G. 46

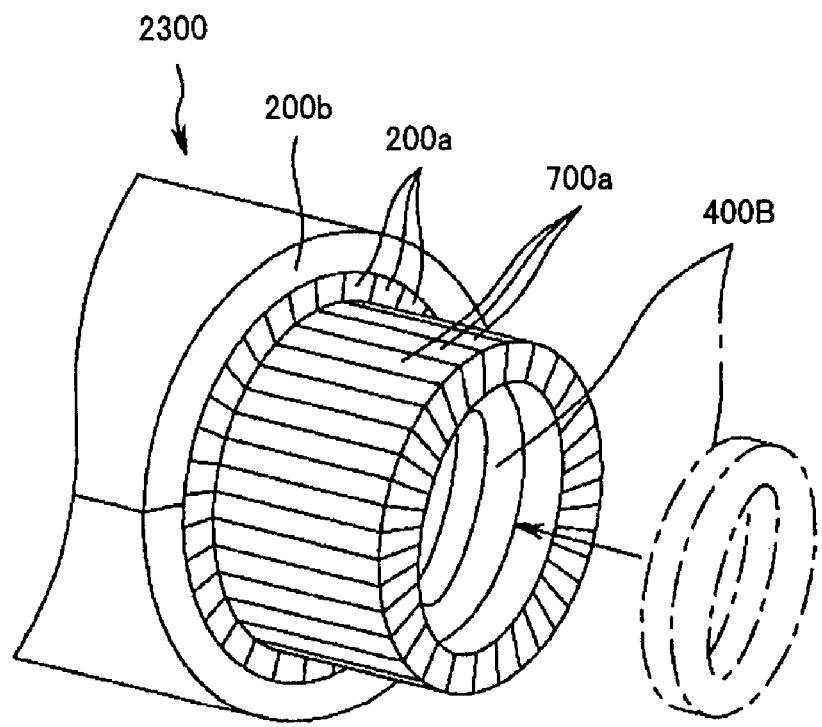
F I G. 47

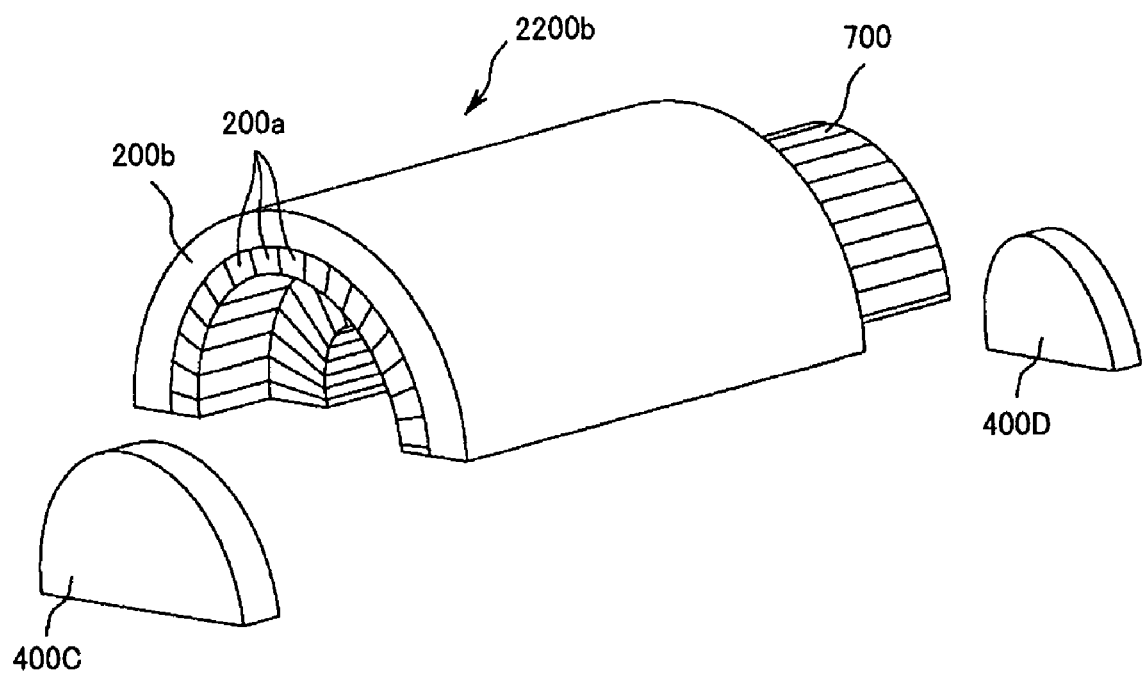
F I G. 4 8

ULTRASONIC TRANSDUCER, ULTRASONIC TRANSDUCER ARRAY AND ULTRASOUND ENDOSCOPE APPARATUS

TECHNICAL FIELD

The present invention relates to an electronic radial scanning type ultrasonic transducer.

BACKGROUND ART

In conventional medical practice there exists an ultrasonic diagnosis apparatus that repeatedly transmits an ultrasonic pulse into a live body from an ultrasonic transducer, then receives an echo of the ultrasonic pulse reflected from the live body by the same or separately equipped ultrasonic transducer, and then gradually shifts the direction of transmission and reception of the ultrasonic pulse, thereby displaying information collected from a plurality of directions within the live body as a visible ultrasonic tomography image.

The ultrasonic transducers used for such an ultrasonic diagnosis apparatus or the like include an array type ultrasonic transducer employing an electronic scanning system that arrays a plurality of piezoelectric elements regularly. This ultrasonic transducer includes a radial array type that arrays a plurality of piezoelectric elements in a cylindrical arrangement, a convex array type that arrays them in roughly a partially cylindrical arrangement, and a linear array type that arrays them in a plate arrangement.

The radial array type ultrasonic transducer has conventionally been produced by sequentially adhering, on a support member formed by a flexible thin plate which has a damper effect, for example, a piezoelectric plate, made of lead zirconate titanate for example, and an acoustic matching layer. This adhering is followed by forming cut-in grooves, leaving the support member in the lower layer uncut, of predetermined pitches perpendicular to the longitudinal direction by a cutting means for constituting an transducer array having a large number of ultrasonic transducers, and by adhering the back surface of the support member structuring the transducer array onto the circumference of a damper member-cum-fix member (also called "backing member") whose cross-section is circular (for an example, refer to patent document 1).

An ultrasonic wave probe has conventionally been produced by equipping both surfaces of a piezoelectric element respectively with an acoustic matching layer and a backside load member made of a deformable material and cut-in grooves are formed at predetermined intervals by a cutting means, starting from the side of the acoustic matching layer down to a part of the backside load member. The backside load member is fixed with an adhesive onto the outer surface of a curvature member that is formed to a desired curvature (for an example, refer to patent document 2).

There is also another ultrasonic array transducer configured by putting a backing member frame on the inside of an acoustic lens, mounting a cable harness board on the inside of the backing member frame, and filling the circumference thereof with the backing member (for an example, refer to patent document 3).

Meanwhile, the electronic scanning type ultrasonic transducer is equipped on a part of an endoscope that is inserted into an abdomen, the use of which makes it possible to extract a clear image of deep organs such as digestive canal walls and the pancreas, gall bladder, etc., with good image quality and without being ill influenced by abdominal gases or bones. The electronic scanning type ultrasonic transducer is constituted by no less than several tens of elements and a number of coaxial cables for transmission and reception equivalent to the number of elements. When connecting an electrode of each element of the electronic scanning type ultrasonic transducer to a signal transmission/reception use coaxial cable, a common method is to solder a core lead of the coaxial cable to a signal electrode of each element and to solder a shield wire of the coaxial cable to a ground electrode of each element.

Electronic scanning type ultrasonic transducers such as that described above that have been utilized for an endoscope include convex types, linear types, and radial types, as noted above. The radial type is for transmitting and receiving an ultrasonic beam around a circumference and is categorized into two systems, a mechanical radial scanning system transmitting and receiving an ultrasonic beam radially by rotating the transducers and an electronic radial scanning system transmitting and receiving an ultrasonic beam radially by arraying a plurality of piezoelectric elements on the circumference of a cylinder and electronically controlling them (for an example, refer to patent document 4).

In the case of producing an electronic radial type ultrasonic transducer, a cylindrical shape must be produced in a manner in which both end surfaces of ultrasonic transducer plates that have been divided into a plurality of ultrasonic transducers (i.e., ultrasonic transducer elements) are aligned, as disclosed by patent document 4.

FIG. 1 is a diagram showing a conventional ultrasound endoscope apparatus.

The ultrasound endoscope apparatus 1000 shown in FIG. 1 comprises a connection part 1010, an operation part 1020, and an insertion part 1030 that comprises a head part 1040.

The connection part 1010 is connected to a display apparatus comprising, for example, a display and/or other such device(s) for displaying images or other such things photographed by an ultra compact camera or other such device equipped on the head part 1040.

The operation part 1020 performs curving operations of the insertion part 1030 in the left, right, up and down directions via operation by a user, for example.

The head part 1040 is equipped with a radial system ultrasonic transducer array constituted by, in addition to the ultra compact camera, a plurality of ultrasonic transducers being lined up continuously in a circular pattern around the insertion axis as the center; a selected ultrasonic transducer from among the plurality thereof of the radial system ultrasonic transducer array transmits or receives an ultrasonic wave. The ultrasonic wave received by the ultrasonic transducer array is converted into an electric signal for being displayed on the display or other such device as an image.

FIG. 2 is an enlarged diagram of the dotted line frame H shown in FIG. 1.

As shown in FIG. 2, the head part 1040 comprises a camera part 1110 equipped with an ultra compact camera, illumination element, et cetera, and an ultrasonic wave part 1111 to be equipped with the radial system ultrasonic transducer array and/or other such device.

FIG. 3 is a diagram exemplifying an ultrasonic transducer array.

The ultrasonic transducer array 1120 shown in FIG. 3 comprises a piezoelectric element 1121, a first acoustic matching layer 1122 and a second acoustic matching layer 1123.

The piezoelectric element 1121, first acoustic matching layer 1122 and second acoustic matching layer 1123 are divided into a plurality thereof by commonly featured grooves, resulting in the constitution of the plurality of ultrasonic transducers. Note that the groove featured commonly for the piezoelectric element 1121, first acoustic matching layer 1122 and second acoustic matching layer 1123 is extended from the upper face of the piezoelectric element 1121 to a part of the second acoustic matching layer 1123 so that the individual ultrasonic transducers are connected to one another by the second acoustic matching layer 1123 according to this comprisal as shown in FIG. 3.

The individual grooves are equipped with division members 1124 (i.e., 1124-1, 1124-2, 1124-3, 1124-4, 1124-5 and so on), respectively. The division members 1124 are constituted by a resin or by particles attenuating an ultrasonic wave, and are constructed by the aforementioned material filling in the grooves that are featured commonly for the piezoelectric element 1121, first acoustic matching layer 1122 and second acoustic matching layer 1123; this is followed by the material being solidified (for an example, refer to patent document 5).

As to the ultrasonic transducer array 1120, the end surfaces in the direction perpendicular to the longitudinal direction of the ultrasonic transducer array 1120 are connected with one another from the state shown in FIG. 3, thereby constructing the radial system ultrasonic transducer array.

FIG. 4 is a diagram showing a constructed radial system ultrasonic transducer array from the ultrasonic transducer array 1120 shown in FIG. 3.

The inside of an opening part of the radial system ultrasonic transducer array 1120 shown in FIG. 4 is equipped with a roughly donut-shaped frame member 1130 that retains the state of the individual ultrasonic transducers of the ultrasonic transducer array 1120 being formed in a circular pattern.

There already exists such a case in which the frame member 1130 is used to retain the form of individual ultrasonic transducers of the ultrasonic transducer array 1120 (for an example, refer to patent document 3).

The electronic radial type ultrasonic transducer is able to perform scans in 360 degrees, and therefore the scan intervals are desirably uniform across all directions.

In order to form the ultrasonic transducer arraying the ultrasonic transducer elements on a plane into a circular shape as described above, however, a side face on one end must be matched with that on the other end in order to roll up the flat-formed ultrasonic transducer into a cylindrical shape, resulting in the creation of a joint part for the electronic radial type ultrasonic transducer.

As shown in FIG. 5, the conventional electronic radial type ultrasonic transducer ends up with a different interval between the adjacent ultrasonic transducer elements in the place at which the ends are joined (joint 2010) in an ultrasonic transducer plate 2000 that is rolled up into a cylindrical shape, and this causes an ill influence on images obtained from the ultrasonic transducer elements encompassing the joint 2010.

Such a joint is unique to electronic radial type transducers and is not seen in the convex type or linear type transducers; therefore special care has conventionally been required in the handling of regions corresponding to the joint when photographing the interior of an abdomen with an ultrasound endoscope that uses an electronic radial type ultrasonic transducer.

The electronic radial type ultrasonic transducer used for an ultrasound endoscope is now being configured to have the outer diameter of the transducer be around 10 mm so that a variation of a few tens of micrometers alters the angle and interval of the adjacent transducer. This causes a significant ill influence on image quality when compared to large scale ultrasonic transducers such as sonar in which a displacement of a few tens of micrometers at a joint is not significant.

A backing member usually uses a soft resin for retaining a damping effect. However, if the joint is adhered with the backing member, durability is undermined when performing sterilization treatment via chemicals or heating. As such, connection of a joint with the backing member material results in varying characteristics and leads to reduced durability due to the use of a flexible material.

Also, in either of the radial system ultrasonic transducer arrays 1120 shown in FIG. 4, the convex system ultrasonic transducer array or the linear system ultrasonic transducer array, a predefined ultrasonic transducer needs to be identified when producing, inspecting or repairing the ultrasonic transducer array.

For the convex system ultrasonic transducer array and the linear system ultrasonic transducer array, a predefined ultrasonic transducer can be identified by registering information on a function of the nth ultrasonic transducer from the one at an end in advance and counting the ultrasonic transducers in sequence from the one at the end.

In an ultrasonic transducer array symmetrically formed for obtaining a good acoustic characteristics such as the radial system ultrasonic transducer array 1120 shown in FIG. 4, the individual ultrasonic transducers are formed into a circular pattern by mutually connecting the ultrasonic transducers at both ends, making it difficult to identify ultrasonic transducers at the ends; this results in a difficulty in identifying a specific ultrasonic transducer.

Also, in the convex system ultrasonic transducer array and linear system ultrasonic transducer array, if an ultrasonic transducer array used for an ultrasound endoscope apparatus is very small, it is difficult to count the ultrasonic transducers and hence difficult to identify a predefined ultrasonic transducer.

Also, the ultrasonic transducer formed by fixing a flexible support member to a damper member with an adhesive, such as the ultrasonic probe noted in patent document 1, has been faced with the possibility of occurrences of performance problems such as an elongated pulse width caused by the adhesive layer being placed in between the support member and the damper member.

Also, in the production method for the ultrasonic wave probe noted in patent document 2, a flexible or deformable elastic member is curved and is fixed to a damper member or curved member with an adhesive, thereby forming a prescribed feature. Because of this, there is a possibility that a residual stress in the elastic member will cause a broken electrical connection or other such failure.

Furthermore, when fixing a soft member with an adhesive, the thickness of the adhesive layer varies and the form of the member cannot be maintained at a high accuracy; this is different from the case of adhering hard members to each other, and therefore it has been difficult to obtain the desired accuracy of the form.

Requirements for the backing member frame include high form accuracy, insulation, the capability of adding a conductor pattern and thermal resistance against heat from soldering in cases in which there is a connection to a lead wire, and other properties. However, common board materials such as glass epoxy board used for the usage described above have been faced with difficulties in improving the accuracy of the machining process because of minute changes in form as a result of the glass fiber coming off the resin at an edge part that is being processed for a feature.

In addition, polyimide has a low rigidity and a low adhesive property, and is thus faced with the problem of being unsuitable for use for a frame.

In consideration of the above described problems, a purpose of the present invention is to provide an electronic radial type ultrasonic transducer that makes all of the environment uniform in relation to a material and in relation to the interval between ultrasonic transducer elements.

Another purpose of the present invention is to provide an ultrasonic transducer array that enables the easy identification of a predefined ultrasonic transducer no matter what system it is categorized as.

Yet another purpose of the present invention is to provide an ultrasonic transducer with a high reliability and strength that is capable of obtaining a good ultrasonic image by preventing occurrences of failure that are due to residual stress and by the highly accurate arraying of divided piezoelectric elements via the use of polyphenylether (PPE) as a frame material. PPE has the characteristics of high thermal resistance, good processability, and good retainability of external features.

Patent document 1: Laid-Open Japanese Patent Application Publication No. H02-271839

Patent document 2: Japanese Registered Patent No. 2502685

Patent document 3: Laid-Open Japanese Patent Application Publication No. 2002-224104

Patent document 4: Japanese Registered Patent No. Sho 63-14623

Patent document 5: Laid-Open Japanese Patent Application Publication No. H10-285695

DISCLOSURE OF INVENTION

In order to solve the problem described above, the present invention adopts the following comprisal.

An electronic radial type ultrasonic transducer according to the present invention is an array, at even intervals and in a cylindrical arrangement, of a plurality of ultrasonic transducer elements that transmit and receive ultrasonic waves. The electronic radial type ultrasonic transducer according to the present invention also is laminated by a plurality of acoustic matching layers, wherein a gap formed on the side face of the ultrasonic transducer element is filled with the same material as that of the acoustic matching layer in the outermost layer.

The electronic radial type ultrasonic transducer may also be configured in such a manner that the gap is approximately the same width as the space between the ultrasonic transducer elements.

The electronic radial type ultrasonic transducer may also be configured in such a manner that a member constituted by the same material as that of the acoustic matching layer in the outermost layer is installed in the gap.

The electronic radial type ultrasonic transducer may also be configured in such a manner that the gap is filled with the member together with an adhesive constituted by the same material as that of the acoustic matching layer in the outermost layer.

The electronic radial type ultrasonic transducer may also be configured in such a manner that the member is installed in a gap part sandwiched by a pair of parts other than the gap between elements transmitting and receiving the ultrasonic wave out of the ultrasonic transducer elements.

An electronic radial type ultrasonic transducer according to the present invention is also one that arrays a plurality of ultrasonic transducer elements, which transmit and receive ultrasonic waves, at even intervals in a cylindrical arrangement and that layers a plurality of acoustic matching layers, wherein a gap formed on the side face of the ultrasonic transducer element is approximately the same length as that of the space between the ultrasonic transducer elements.

A production process of an electronic radial type ultrasonic transducer according to the present invention comprises: a body structure production process for producing a body structure that arrays a plurality of ultrasonic transducer elements which transmits and receives ultrasonic waves, and layers a plurality of acoustic matching layers; a cylinder forming process for forming the body structure into a cylindrical shape by bringing first and a second side faces of the body structure face to face with each other; a member insertion process for inserting a member constituted by the same material as that of the acoustic matching layer in the outermost layer into a gap between the first and second side faces of the cylindrically shaped body structure; a circular member installation process for installing a circular member on the inside of an opening part of the cylindrically shaped body structure; a cable harnessing process for leading a plurality of cables through a roughly cylindrical shaped insulation member provided with a flange on one end and connecting one end of each of the cables respectively to a plurality of electrode pads that are equipped on the flange surface of the insulative member; an insulative member insertion process for inserting the insulative member into the body structure until the flange of the insulative member obtained by the cable harnessing process comes into contact with the circular member of the structure member obtained by the circular member installation process; and a connection process for connecting, with wire, the electrode pad equipped on the flange surface of the insulative member (this electrode pad is inserted in the insulative member insertion process) to the electrodes of the ultrasonic transducer elements.

The scope of the present invention encompasses an ultrasound endoscope comprising the above-noted electronic radial type ultrasonic transducer.

An ultrasonic transducer array according to the present invention is one comprising a plurality of ultrasonic transducers featuring a plurality of grooves on a plate-formed piezoelectric element, wherein ultrasonic waves are transmitted or received by an ultrasonic transducer selected from the plurality of ultrasonic transducers, wherein the plurality of grooves are respectively equipped with division members and the color of a division member adjacent to a predetermined ultrasonic transducer from among the individual division members is different from that of the other division members.

An ultrasonic transducer array according to the present invention is also one comprising a plurality of ultrasonic transducers featuring a plurality of grooves in a plate-formed piezoelectric element and a frame member in contact with all of the plurality of ultrasonic transducers and retaining the form thereof, wherein an ultrasonic wave is transmitted or received by an ultrasonic transducer selected from the plurality of ultrasonic transducers, wherein the plurality of grooves are respectively equipped with division members and the color of a division member adjacent to a predetermined ultrasonic transducers from among the individual division members is different from that of the other division members, and a mark for indicating the position of the predefined ultrasonic transducer is attached to the frame member close thereto.

The ultrasonic transducer array may also be configured in such a manner that the color of a division member adjacent to the predefined ultrasonic transducer from among the individual division members is different from that of the other division members as a result of the division member mixed with a colorant being hardened after it is filled in the groove adjacent to the predefined ultrasonic transducer, or of the division member, from which the colorant is removed, being hardened after it is filled in the groove adjacent to the predefined ultrasonic transducer.

The ultrasonic transducer array may also be configured in such a manner that the color of a division member adjacent to the predefined ultrasonic transducer from among the individual division members is different from that of the other division members as a result of a plate-shaped division member having a different color from that of the other division members being inserted into the groove adjacent to the predefined ultrasonic transducer.

The division member of the ultrasonic transducer array may also be configured to be colored differently in different parts.

An ultrasonic transducer array according to the present invention is one comprising a plurality of ultrasonic transducers featuring a plurality of grooves of a plate-shaped piezoelectric element and a frame member in contact with all of the plurality of ultrasonic transducers and retaining the shape thereof, wherein ultrasonic waves are transmitted or received by an ultrasonic transducer selected from among the plurality of ultrasonic transducers, wherein a mark for indicating the position of the predefined ultrasonic transducer is attached to the frame member close thereto.

The predefined ultrasonic transducer of the ultrasonic transducer array may also be configured to be constituted by a plurality of ultrasonic transducers having the same characteristic or function.

An ultrasonic transducer array according to the present invention is one comprising a plurality of ultrasonic transducers featuring a plurality of grooves in a plate-shaped piezoelectric element, wherein ultrasonic waves are transmitted or received by an ultrasonic transducer selected from among the plurality of ultrasonic transducers, wherein the plurality of ultrasonic transducers is formed into a circular arrangement by two ultrasonic transducers from among the plurality of ultrasonic transducers being connected together by a connection member, the color of which being different from that of division members respectively installed in the plurality of grooves.

An ultrasound endoscope apparatus according to the present invention is equipped with an ultrasonic transducer array comprising a plurality of ultrasonic transducers featuring a plurality of grooves in a plate-shaped piezoelectric element, wherein an ultrasonic wave is transmitted or received by an ultrasonic transducer selected from among the plurality of ultrasonic transducers, wherein the plurality of grooves are respectively equipped with division members and the color of a division member adjacent to a predetermined ultrasonic transducer from among the individual division members is different from that of the other division members.

An ultrasonic transducer according to the present invention comprises: an acoustic matching layer including a hard layer; a piezoelectric body that is shorter than the acoustic matching layer in length, is placed fixedly at a predetermined position in the hard layer and is divided into a plurality of piezoelectric elements by a cutting means, with the piezoelectric body being placed fixedly; and an transducer shape forming member made of a fiber-reinforced thermosetting polyphenylether (PPE) that is placed fixedly, with a surface of the divided piezoelectric element being placed on the internal circumference side, on a surface of the acoustic matching layer on which the piezoelectric elements are placed, with the surface of the acoustic matching layer projecting from the piezoelectric element, thereby arraying a plurality of piezoelectric elements in a predefined form.

Also, an ultrasonic transducer according to the present invention comprises: an acoustic matching layer including a hard layer; a piezoelectric body that is shorter than the acoustic matching layer in length, that is placed fixedly at a predetermined position of the hard layer, and that is divided into a plurality of piezoelectric elements by a cutting means, with the piezoelectric elements being placed fixedly; an transducer shape forming member made of a hard material that is placed fixedly, with a surface of the divided piezoelectric elements being placed on the internal circumference side, on a surface of the acoustic matching layer on which the piezoelectric elements are arranged, with the acoustic matching layer projecting from the piezoelectric element, thereby arraying a plurality of piezoelectric elements in a predefined form; and an insulative member that is placed on the outside of the transducer shape forming member and is made of a fiber reinforced thermosetting PPE for electrically insulating a conductive member from the outside.

Also, an ultrasonic transducer according to the present invention comprises: an acoustic matching layer formed by layering at least a hard first acoustic matching layer and a soft second acoustic matching layer; a piezoelectric body that is shorter than the acoustic matching layer in length, is placed fixedly at a predetermined position of the first acoustic matching layer, and is divided into a plurality of piezoelectric elements by a cutting means, with the piezoelectric elements being placed fixedly; and an transducer shape forming member constituted by a fiber-reinforced thermosetting PPE that is placed fixedly, with a surface of the divided piezoelectric element being placed on the internal circumference side, on a surface of the first acoustic matching layer constituting the acoustic matching layer that projects from the piezoelectric element, thereby arraying a plurality of piezoelectric elements in a predefined form.

Also, an ultrasonic transducer according to the present invention comprises: an acoustic matching layer formed by layering at least a hard first acoustic matching layer and a soft second acoustic matching layer; a piezoelectric body that is shorter than the acoustic matching layer in length, that is placed fixedly at a predetermined position of the first acoustic matching layer, and that is divided into a plurality of piezoelectric elements by a cutting means, with the piezoelectric elements being placed fixedly; an transducer shape forming member of a hard material that is placed fixedly, with a surface of the divided piezoelectric element being placed on the internal circumference side fixedly, on a surface of the first acoustic matching layer constituting the acoustic matching layer projecting from the piezoelectric element, thereby arraying a plurality of piezoelectric elements in a predefined form; and an insulative member that is placed on the outside of the transducer shape forming member and is made of a fiber-reinforced thermosetting PPE for electrically insulating a conductive member from the outside.

Also, the ultrasonic transducer according to the present invention is preferably configured in such a manner that the piezoelectric elements are formed by providing division grooves at predefined intervals that start from the surface of a piezoelectric body placed fixedly on the first acoustic matching layer, and then pass the layer by the cutting means to reach the second acoustic matching layer.

Also, the ultrasonic transducer according to the present invention is preferably configured in such a manner that the transducer shape forming member is circular.

Also, the ultrasonic transducer according to the present invention is preferably configured in such a manner that the insulative member is circular.

Also, the ultrasonic transducer according to the present invention is preferably configured in such a manner that the transducer shape forming member is roughly a partial cylinder.

Also, the ultrasonic transducer according to the present invention is preferably configured in such a manner that the insulative member is roughly a partial cylinder.

Also, an ultrasonic transducer according to the present invention comprises: an acoustic matching layer including a hard layer; a piezoelectric body that is placed fixedly, in a positional relationship that a part of the acoustic matching layer projects from the piezoelectric body, onto a predetermined position in a hard layer constituting the acoustic matching layer, and that is provided with one-face-side electrode and an other-face-side electrode respectively on each side of the flat parts divided into a plurality of piezoelectric elements by a cutting means, with the piezoelectric body being placed fixedly; and an transducer shape forming member constituted by a fiber-reinforced thermosetting PPE that is placed fixedly, with a surface of the piezoelectric element that is divisionally formed being placed on the internal circumference side, onto a surface of the first acoustic matching layer constituting the acoustic matching layer projecting from the piezoelectric element, thereby arraying a plurality of piezoelectric elements in a predefined arrangement. In this predefined arrangement, a band-shaped conductive material of a predetermined width is equipped at a predetermined position on an end side of the acoustic matching layer, in parallel with the piezoelectric body and facing an electrode featured on a flat part of the piezoelectric body, while the transducer shape forming member is equipped with a conductive part that is placed facing a conductive component extensively placed from the piezoelectric body.

Also, an ultrasonic transducer according to the present invention comprises: an acoustic matching layer including a hard layer; a piezoelectric body that is placed fixedly, in a positional relationship that a part of the acoustic matching layer projects from the piezoelectric body, onto a predetermined position of a hard layer constituting the acoustic matching layer, and that provides one-face-side electrode and an other-face-side electrode respectively on each side of the flat parts divided into a plurality of piezoelectric elements by a cutting means with the piezoelectric elements being placed fixedly; an transducer shape forming member made of a hard material that is placed fixedly, with a surface of the piezoelectric element, which is divisionally formed, being placed on an internal circumference side fixedly, onto a surface on which the piezoelectric element of the acoustic matching layer projects from the piezoelectric element, thereby arraying a plurality of piezoelectric elements in a predefined arrangement; and an insulative member that is placed on the outside of the transducer shape forming member and that is made of a fiber-reinforced thermosetting PPE for electrically insulating a conductive member from the outside, wherein a band-shaped conductive component of a predetermined width is equipped at a predetermined position on an end side of the acoustic matching layer, in parallel with the piezoelectric body and facing an electrode featured on a flat part of the piezoelectric body, while the transducer shape forming member is equipped with a conductive part facing a conductive component extensively placed from the piezoelectric body.

The ultrasonic transducer according to the present invention is preferably configured in such a manner that electrical conduction of at least one of the following two places is carried out; conduction in one possible place is carried out by contacting an electrode equipped on a flat part of the piezoelectric body to a band-shaped conductive component equipped on the acoustic matching layer, while conduction in another possible place is carried out by contacting the conductive component to a conductive part of the transducer shape forming member.

The ultrasonic transducer according to the present invention is preferably configured in such a manner that electrical conduction of at least one of the following two places is carried out by way of a conductive member; conduction in one possible place is carried out by contacting an electrode equipped on a flat part of the piezoelectric body to a band-shaped conductive component equipped on the acoustic matching layer, while conduction in another possible place is carried out by contacting a conductive component to a conductive part of the transducer shape forming member.

The ultrasonic transducer according to the present invention is preferably configured in such a manner that the conductive member is either a metallic grazing member, a conductive adhesive, conductive painting or a conductive film.

The electronic radial type ultrasonic transducer according to the present invention is also preferably configured in such a manner that the width of the member is smaller than the space between the ultrasonic transducer elements.

The production process of an electronic radial type ultrasonic transducer according to the present invention is also such that the member insertion process coats, on a surface of the member, an adhesive constituted of the same material as that of the acoustic matching layer in the outermost layer, and then inserts the member into the gap.

BRIEF DESCRIPTION OF DRAWINGS

FIG. 4 is a diagram showing a radial system ultrasonic transducer array;

FIG. 8 is a diagram showing a production process of an ultrasonic transducer (part 1);

FIG. 16A is a diagram showing a production process of an ultrasonic transducer (part 7);

FIG. 16B is a diagram showing a production process of an ultrasonic transducer (part 7);

FIG. 17 is a diagram showing a production process of an ultrasonic transducer (part 8);

FIG. 21 is a diagram showing an ultrasonic transducer array according to another preferred embodiment of the present invention;

FIG. 27 is a diagram showing a radial system ultrasonic transducer array according to another preferred embodiment of the present invention;

FIG. 29 is a cross-sectional diagram in the longitudinal direction describing a comprisal of an ultrasonic transducer;

FIG. 33 is a diagram describing another configuration example of the part indicated by arrow B in FIG. 29;

FIG. 34 is an enlarged diagram of the part indicated by arrow C in FIG. 29;

FIG. 35 is a diagram describing members for forming an acoustic matching layer;

FIG. 36 is a diagram describing an acoustic matching layer;

FIG. 38 is a diagram describing the first layer body;

FIG. 42 is a diagram showing an appearance of dividing piezoelectric ceramics into piezoelectric elements by forming division grooves;

FIG. 44 is a diagram showing the deformation of a second layer body that has a plurality of piezoelectric elements;

FIG. 45 is a diagram describing members used for forming a cylindrically formed transducer unit;

FIG. 46 is a diagram showing the placing of an transducer shape forming member on a first acoustic matching layer;

FIG. 47 is a diagram showing the placing an transducer shape forming member on a board;

FIG. 48 is a diagram showing an transducer shape forming member and a second layer body used for forming a convex array type transducer unit;

BEST MODE FOR CARRYING OUT THE INVENTION

Figure 6:
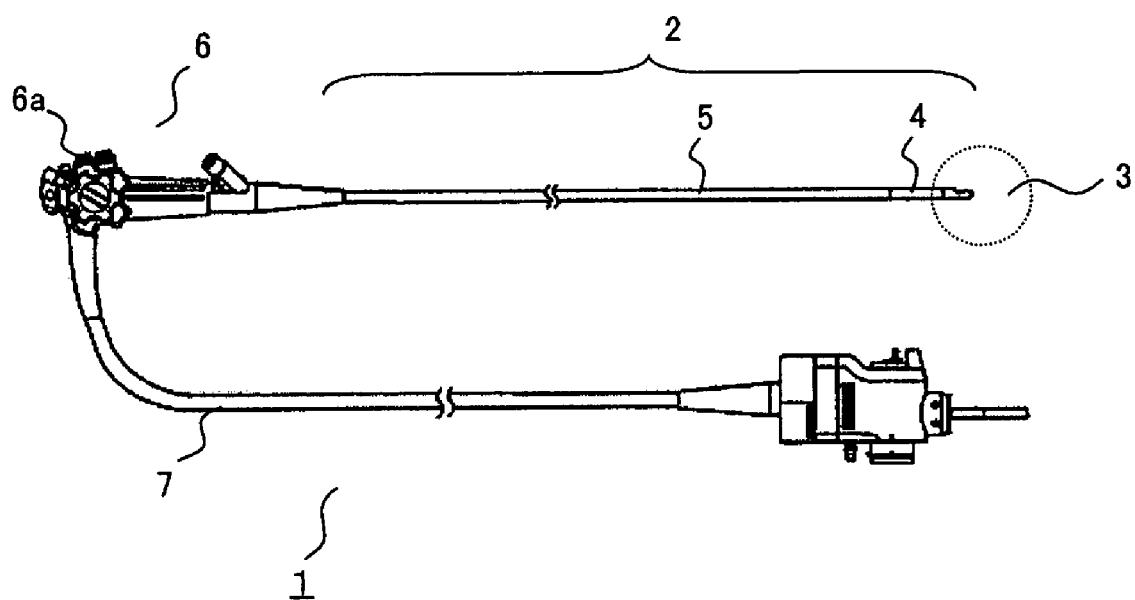
FIG. 6 is a diagram showing an external configuration of an ultrasound endoscope according to the present embodiment.

FIG. 6 is a diagram showing an external configuration of an ultrasound endoscope according to the present embodiment. The ultrasound endoscope 1 comprises an operation part 6 on the base end of a slender insertion part 2. A universal cord 7 to be connected to a light source apparatus (not shown herein) extends from the side part of the operation part 6.

The insertion part 2 comprises the connection of, in sequence starting at the head part, a head part 3, a bendable part 4 allowing the insertion part to bend freely, and a flexible tube part 5 having flexibility. The operation part 6 is equipped with a bending operation knob 6a so that the bendable part 4 can be bent by operating the bending operation knob 6a.

Figure 7:
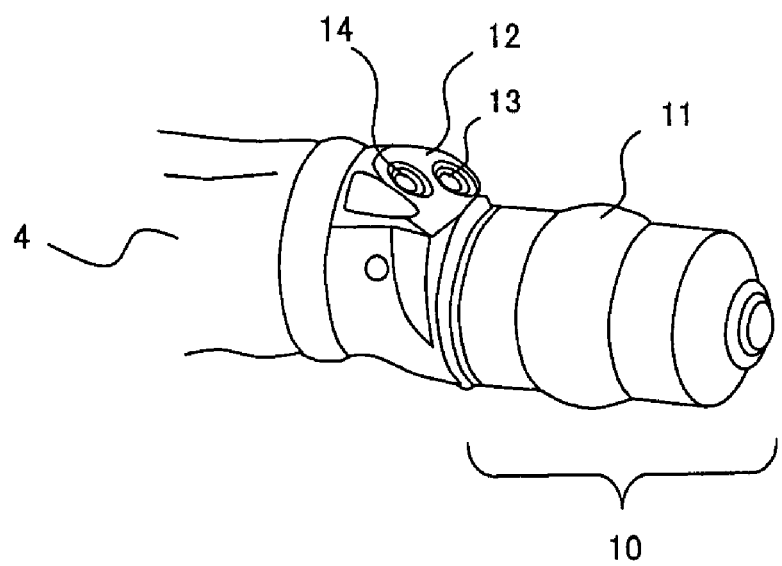
FIG. 7 is an enlarged diagram of a head part 3 of an ultrasound endoscope shown in FIG. 6.

FIG. 7 is an enlarged diagram of the head part 3 of the ultrasound endoscope 1 shown in FIG. 6. The head part 3 is equipped with an ultrasonic transducer 10 (or an ultrasonic transducer array) enabling electronic radial type scanning, and an inclined part 12 is formed between the bendable part 4 and the ultrasonic transducer 10. The ultrasonic transducer 10 is covered with a material, forming an acoustic lens 11. The inclined part 12 is equipped with an illumination lens cover (not shown herein) constituting an illumination optical system for emitting an illuminating light to an observation region, an observation-use lens cover 13 constituting an observation optical system for acquiring an optical image of an observation region and a forceps exit hole 14 that is an opening for projecting a treatment instrument.

Next, a description is given of a production process of the ultrasonic transducer 10 according to the present embodiment by using FIGS. 8 through 18.

FIG. 8 is a diagram showing a production process of an ultrasonic transducer (part 1). Referring to FIG. 8, in the first step the ultrasonic transducer produces body structure A comprising a board 20, a conductive body 21, electrodes 22 (i.e., 22a and 22b), a piezoelectric element 23, acoustic matching layers 24 (i.e., first and a second matching layers 24a and 24b, respectively), a conductive resin 25 and grooves 26. To begin with, production of body structure A is described.

The second matching layer 24b is produced first, followed by the first matching layer 24a. Next, the grooves in the first matching layer 24a are made using, for example, a dicing saw (i.e., a high precision shearing machine), followed by the pouring of conductive resin 25 into the grooves. Next, a piezoelectric element 23 that has the electrodes 22a and 22b respectively on both of the opposite principal faces is joined to the layers, then a board 20 is mounted adjacent to the side of the piezoelectric element 23. The surface of the board 20 has an electrode layer 20a. Next, the conductive body 21 for electrically connecting the electrode 22a to the electrode layer 20a is mounted.

Next, a plurality of grooves (i.e., diced grooves) 26 of several tens of micrometers in width are created using a dicing saw for cutting into body structure A that is formed as described above. The width of each of these grooves is desirably between 20 and 50 micrometers. Note that the cutting of the body structure A leaves uncut several tens of micrometers of the thickness of the second matching layer 24b. Approximately 200 such grooves are cut. Here, the divided transducers are called ultrasonic transducer elements 27.

Note that the present embodiment as described above is of a two-layer matching type, and therefore the material for the first acoustic matching layer 24a preferably uses an epoxy resin containing a filler such as alumina or titania ($TiO_2$), and the material of the second acoustic matching layer 24b is preferably an epoxy resin not containing any filler. In the case of a three-layer matching type, the material for the first acoustic matching layer preferably uses machinable ceramics or a carbon or epoxy resin containing filler or fibers, that of the second acoustic matching layer preferably uses an epoxy resin containing a very small amount (i.e., a lower rate of content as compared to the case of two-layer matching) of a filler such as alumina or titania, and that of the third acoustic matching layer preferably uses an epoxy resin not containing a filler.

Figure 9:
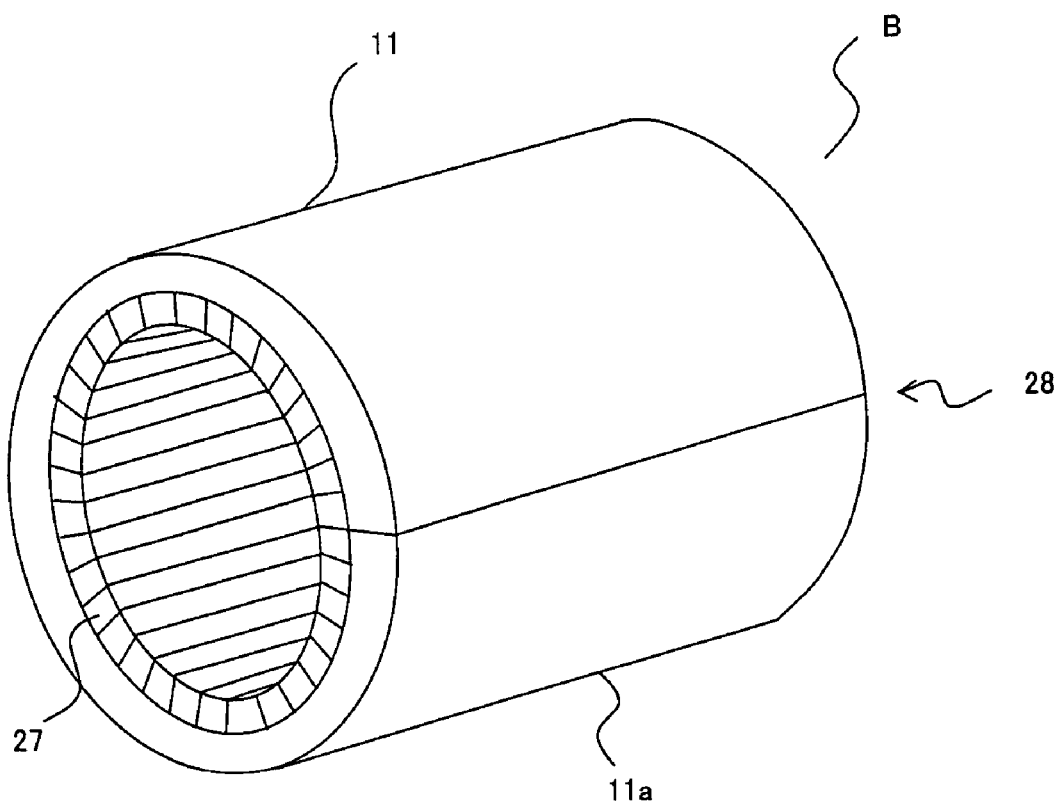
FIG. 9 is a diagram showing a production process of an ultrasonic transducer (part 2)

Next, body structure A is curved and formed into a cylindrical shape in such a manner that the side face X1 is opposite to the side face X2 of the layered body, as shown in FIG. 9. Specifically, body structure A is sandwiched by two molds, each of which has a semi-cylindrical concavity, and is gradually squeezed so as to form the body structure into a cylindrical form. This causes the opposite faces to approach each other, and therefore the squeezing is stopped when the distance between the joint faces becomes a prescribed interval (e.g., is close to the width of the diced groove).

Here, a spacer is prepared in advance by means of an injection molding method. The width of the spacer is configured to be a little smaller than that of the diced groove (e.g., the spacer width is approximately 15 micrometers if the diced groove width is approximately 25 micrometers; or the spacer width is approximately 40 micrometers if the diced groove width is approximately 50 micrometers). In addition, the spacer uses the same resin as that of the outermost acoustic matching layer (i.e., the same resin as that of the second matching layer in the case of two-layer matching, and likewise that of the third matching layer in the case of three-layer matching).

Next, the same resin as that of outermost acoustic matching layer (i.e., the same resin as that of the second matching layer in the case of two-layer matching, and likewise that of the third matching layer in the case of three-layer matching) is coated as an adhesive on both side surfaces of the spacer in the shorter direction.

Figure 10A:
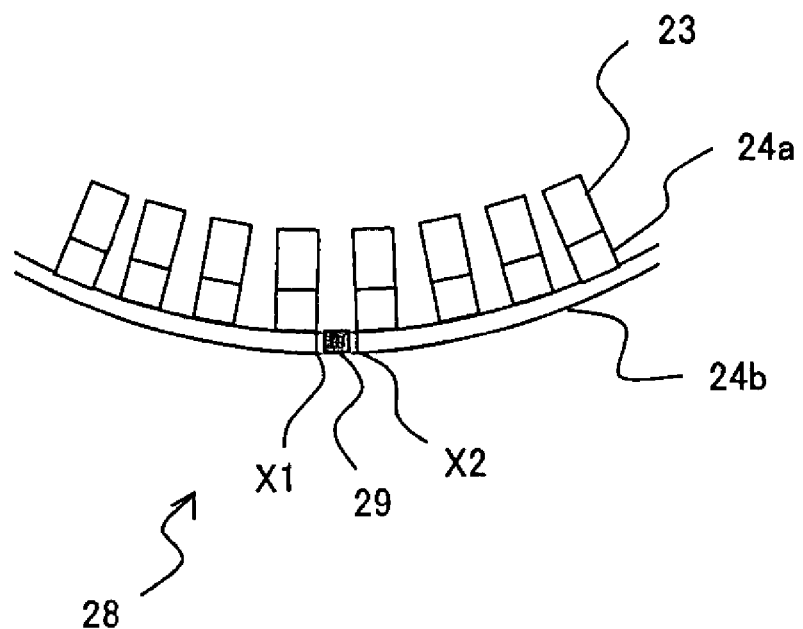
FIG. 10A is an enlarged diagram of a joint part 28 shown in FIG. 9.
Figure 10B:
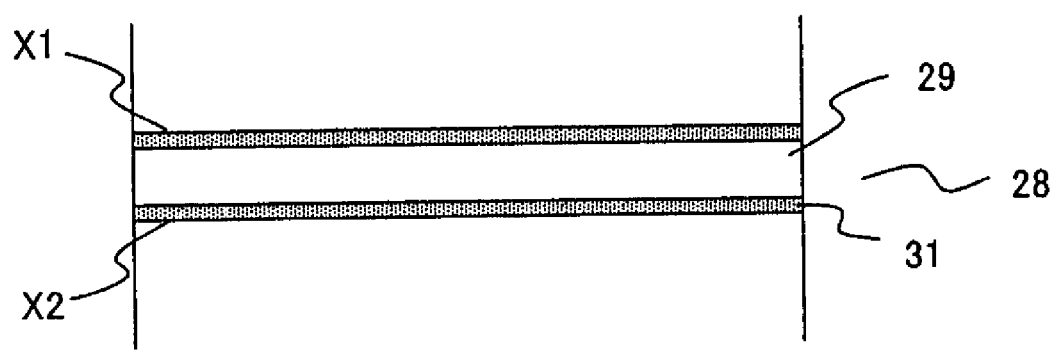
FIG. 10B is an enlarged diagram of a joint part 28 shown in FIG. 9.

Next the spacer 29 is inserted into the joint part 28 (i.e., between the side faces X1 and X2) as shown in FIG. 10, followed by further squeezing of the two molds again.

Figure 11:
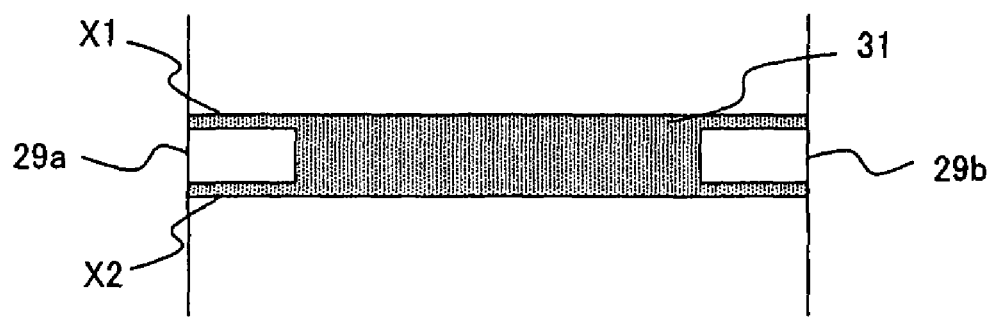
FIG. 11 is a diagram showing another example of applying a spacer to a joint part.

Note that the spacer is sandwiched by the entire surface of the joint faces in the embodiment described above; the spacer, however, may alternatively be partially sandwiched as shown in FIG. 11. According to the configuration of FIG. 11, spacers 29a and 29b may be inserted between both ends of the side faces X1 and X2 that do not actually constitute a drive part (i.e., a piezoelectric element 23), so that the same resin as that of the uppermost layer of the outermost acoustic matching layer (i.e., the same resin as that of the second matching layer in the case of two-layer matching, and likewise that of the third matching layer in the case of three-layer matching) is filled in between the spacers 29a and 29b as the adhesive 31. This configuration makes it possible to reduce influences such as the reflection and attenuation of an ultrasonic wave at a boundary as compared to the case of using a spacer on the entire surface.

The use of the spacer as described above makes it difficult to allow an extraneous gap at the time of molding, making it easy to match the position of the joint part (that is, in the case of a spacer not existing, the joint faces do not come into contact, and instead there is a possibility of either face going into the inside of the cylinder. This positioning is actually capable of accommodating control on the order of 10 micrometers. Note that the squeezing for the molding may be tightened by preparing a plurality of molds in different sizes for changing from a larger sized mold to a smaller sized mold. Alternately, another method may be employed and is not specifically limited.

Figure 12:
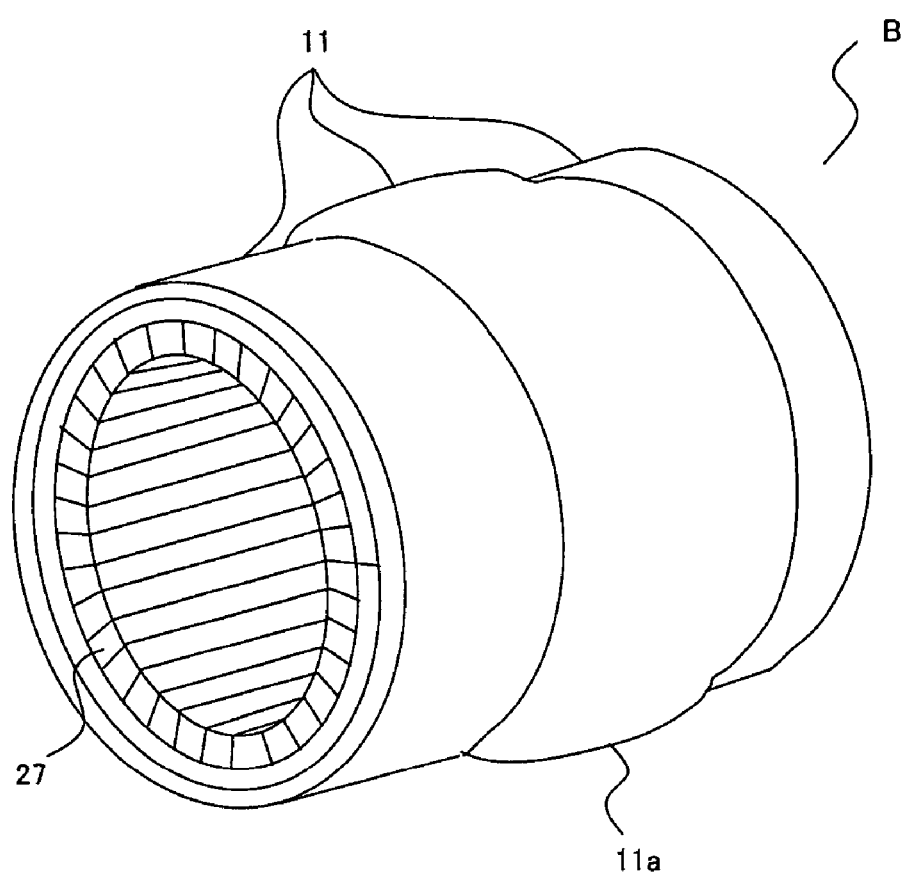
FIG. 12 is a diagram showing a production process of an ultrasonic transducer (part 3)

Once the spacer is mounted onto the joint part 28, the acoustic lens 11 is formed on the surface of the cylinder as shown in FIG. 12 (the resultant form is named "body structure B" hereinafter). As to the acoustic lens 11, one produced in advance as a single acoustic lens body may be combined with the cylindrically shaped body structure A, or one may be produced by placing the cylindrically formed body structure A in a mold, followed by the injection of an acoustic lens material thereinto. Note that lens part 11a of the acoustic lens 11 actually functions as an acoustic lens.

Figure 13:
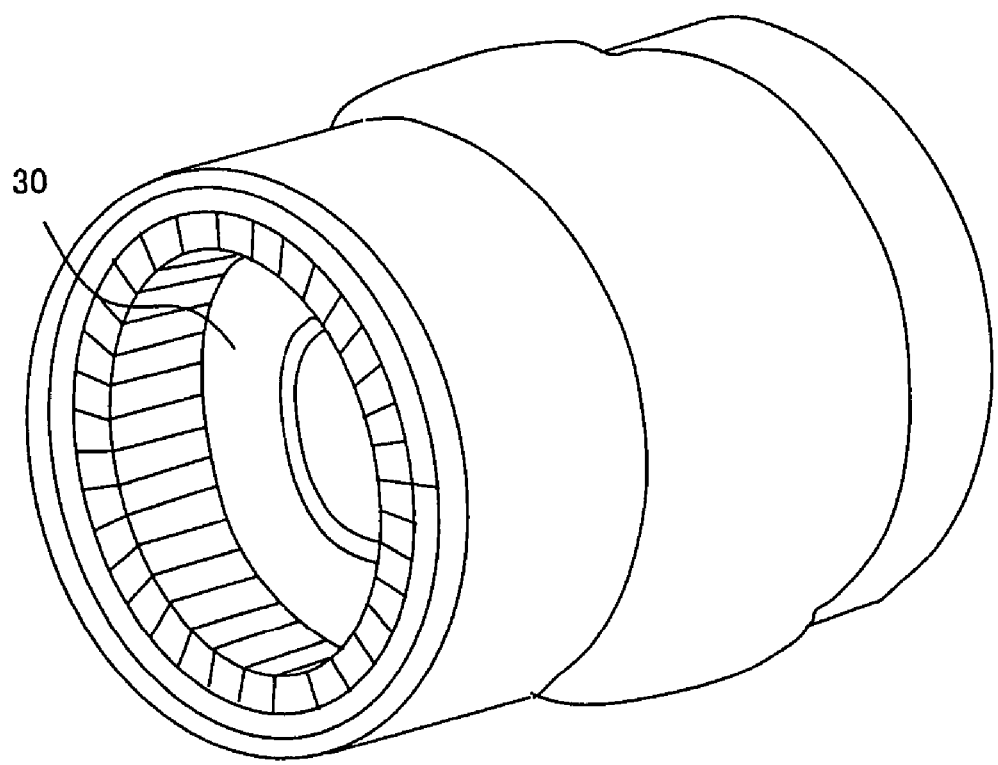
FIG. 13 is a diagram showing a production process of an ultrasonic transducer (part 4)

Next, a circular structure member 30a is mounted on the inside of an opening part of body structure B as shown in FIG. 13. In this situation, the structure member 30a is mounted so as to be positioned on the board 20 (refer to FIG. 14A). Likewise, a structure member 30b is mounted onto the opening part on the other side. In this situation, the structure member 30b is mounted to be positioned on the conductive resin 25 (refer to FIG. 14A).

Figure 14A:
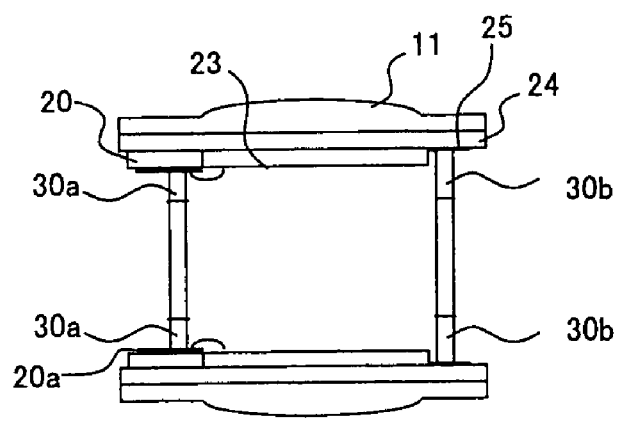
FIG. 14A is a diagram showing a production process of an ultrasonic transducer (part 5)
Figure 14B:
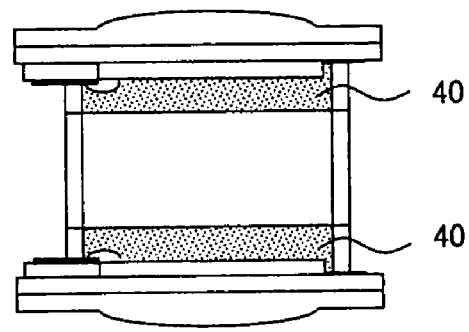
FIG. 14B is a diagram showing a production process of an ultrasonic transducer (part 5)
Figure 14C:
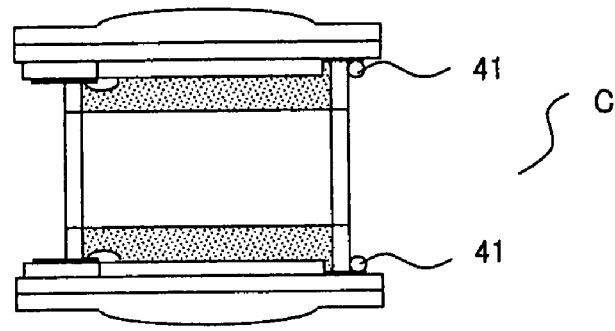
FIG. 14C is a diagram showing a production process of an ultrasonic transducer (part 5)

FIG. 14B shows a cross-section of body structure B with the structure members 30 mounted. The mounting of the structure members 30 (i.e., 30a and 30b) in FIG. 13 (refer to FIG. 14A) is followed by filling the space between the structure members 30a and 30b with a backing member 40 (refer to FIG. 14B). The backing member uses a gelatinous epoxy resin mixed with alumina filler. Next, a conductive body (i.e., a copper wire) 41 is mounted on the conductive resin 25 (refer to FIG. 14C) (the body structure produced as shown in FIG. 14C is named "body structure C" hereinafter).

Figure 15:
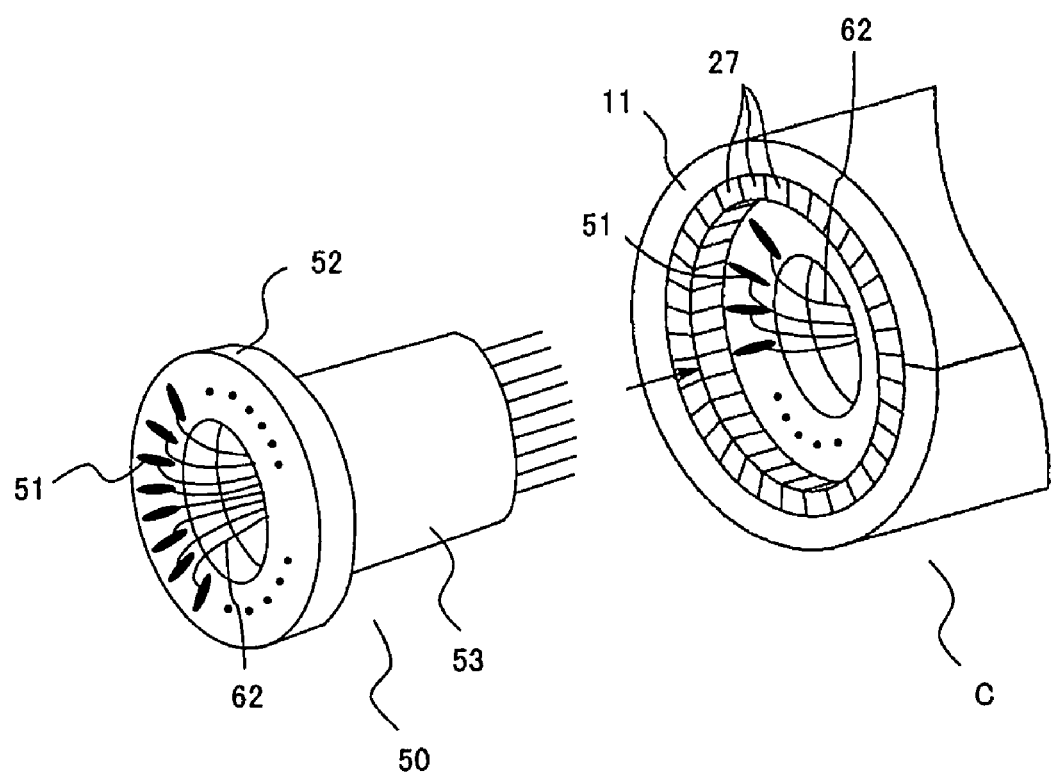
FIG. 15 is a diagram showing a production process of an ultrasonic transducer (part 6)

Next, a cylindrically formed cylinder member 50 is inserted from one opening part side of the body structure C (i.e., the side equipped with the board 20), as shown in FIG. 15. The cylinder member 50 is constituted by a cylinder part 53 and a circular flange 52 featured toward an end thereof. The surface of the flange 52 is equipped with a flexible printed circuit (FPC) board, of which the surface is equipped with several tens to hundreds of electrode pads 51. Furthermore, a cable bundle 62 is internally led though the cylindrical structure member 50 and its tip is soldered to each electrode pad 51 (i.e., the cable 62 is connected by soldering on the inside (i.e., toward the center of circle) of the electrode pad 51). Note that the cable 62 is usually a coaxial cable for noise reduction.

The cylindrical member 50 is made of an insulator material (e.g., engineering plastics). The insulator material may include polysulfone, polyether imide, polyphenylene oxide, and/or epoxy resin, for example.

When inserting the cylindrical member 50 thus connected to the cable 62 into the body structure C (refer to FIG. 16A), the flange 52 part of the cylindrical member 50 hits the structure members 30 of the body structure C, fixing the position of the cylindrical structure member 50, and thus positioning it on the inside of the ultrasonic transducer (refer to FIG. 16B).

FIG. 17 shows the situation of connecting the electrode 20a of the transducer element 27 to the outer side of the electrode pad 51 (i.e., the electrode pad part on the outer circumference of the circle) with a wire 90 after the cylindrical structure member 50 is inserted and positioned (refer to FIG. 16).

Figure 18:
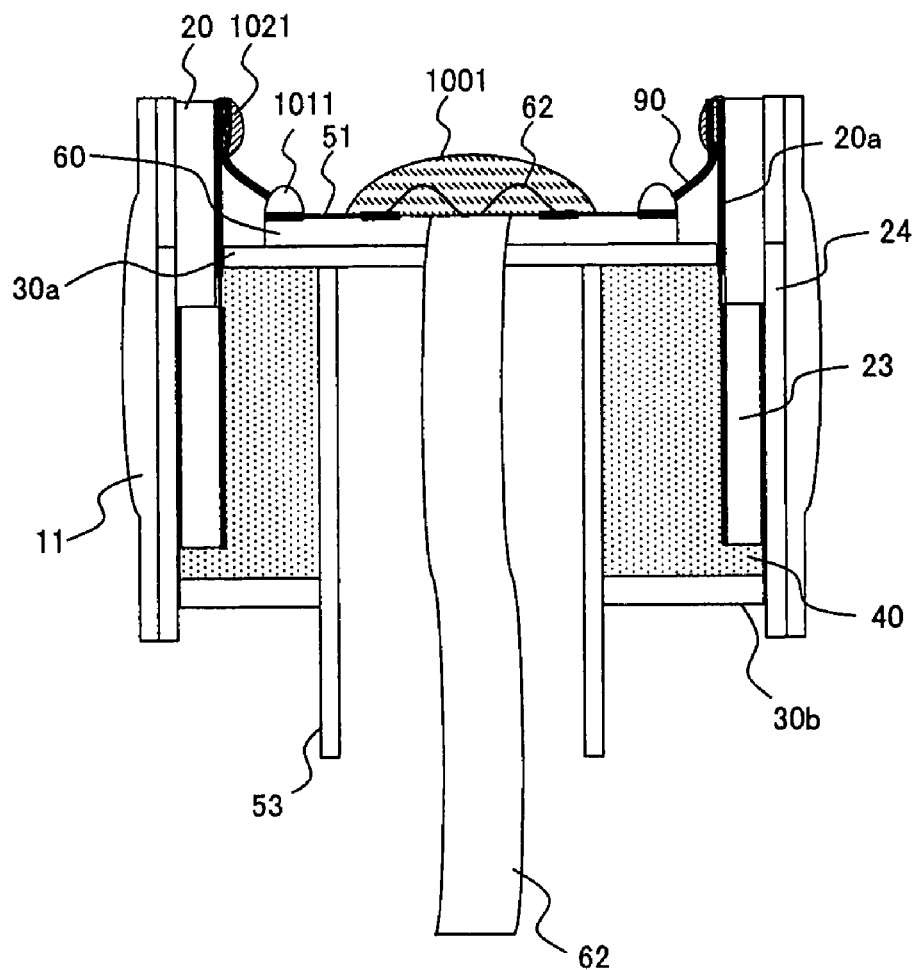
FIG. 18 is a diagram showing a cross-sectional diagram of FIG. 17.

FIG. 18 shows a cross-sectional diagram of FIG. 17. As described above, the cable 62 is connected to the center side portion of the flange of the electrode pad 51 via soldering. One end of a wire 90 is connected to the outer side portion of the flange of the electrode pad 51 via soldering 1011, while the other end is connected to the signal-side electrode 20a existing on the board 20 of the transducer element via soldering 1021. Note that the aforementioned connection is carried out with a short wire 90 for preventing electrical short circuits; the short wire 90 contacts the adjacent signal-side electrode 20a. Next, the entirety of the connection part between the cable 62 and electrode pad 51 is covered with a potting resin 1001 in order to prevent the cable 62 from coming off the electrode pad 51 if the cable 62 is pulled by a load applied thereto.

Note that the spacer may be colored white by adding titanium oxide to the spacer material so as to enable the recognition of a spot thereof. Such a configuration makes it easy to discern the first element (i.e., an element at a joint part).

As described above, the use of the same material, to function as the spacer, as that of the acoustic matching layer on the outermost layer at the joint part (i.e., the connection spot) when forming an ultrasonic transducer into a cylindrical shape, and the adjustment of the spacer width in order to make the width of the joint part the same as that of the diced groove, to make the width between the ultrasonic transducer elements and material environment even, and to thus enable the transmission and reception of ultrasonic waves like the other part, thereby eliminating fluctuations in the acoustic characteristic and improving the acoustic characteristic.

In the case of applying a high temperature sterilization process such as autoclaving to an endoscope used for a treatment, a difference in materials at the joint part may cause a risk of cracking due to different stress levels resulting from the different thermal expansion coefficients of the individual materials. The use of the same material for all components at the joint part according to the present invention prevents biased stress and accordingly prevents the possibility of cracks. The durability of the ultrasonic transducer is therefore improved.

Also, a uniform image quality can be obtained over 360 degrees because the influence of the joint part is limited to the minimum. Positioning is easy because the width of the joint part is adjusted by the spacer. Practically, it can be adjusted to a precision on the order of 10 micrometers. A recognition of the first element (i.e., the element at the joint part) is no longer required since both the intervals and the material between elements are all the same.

Figure 19:
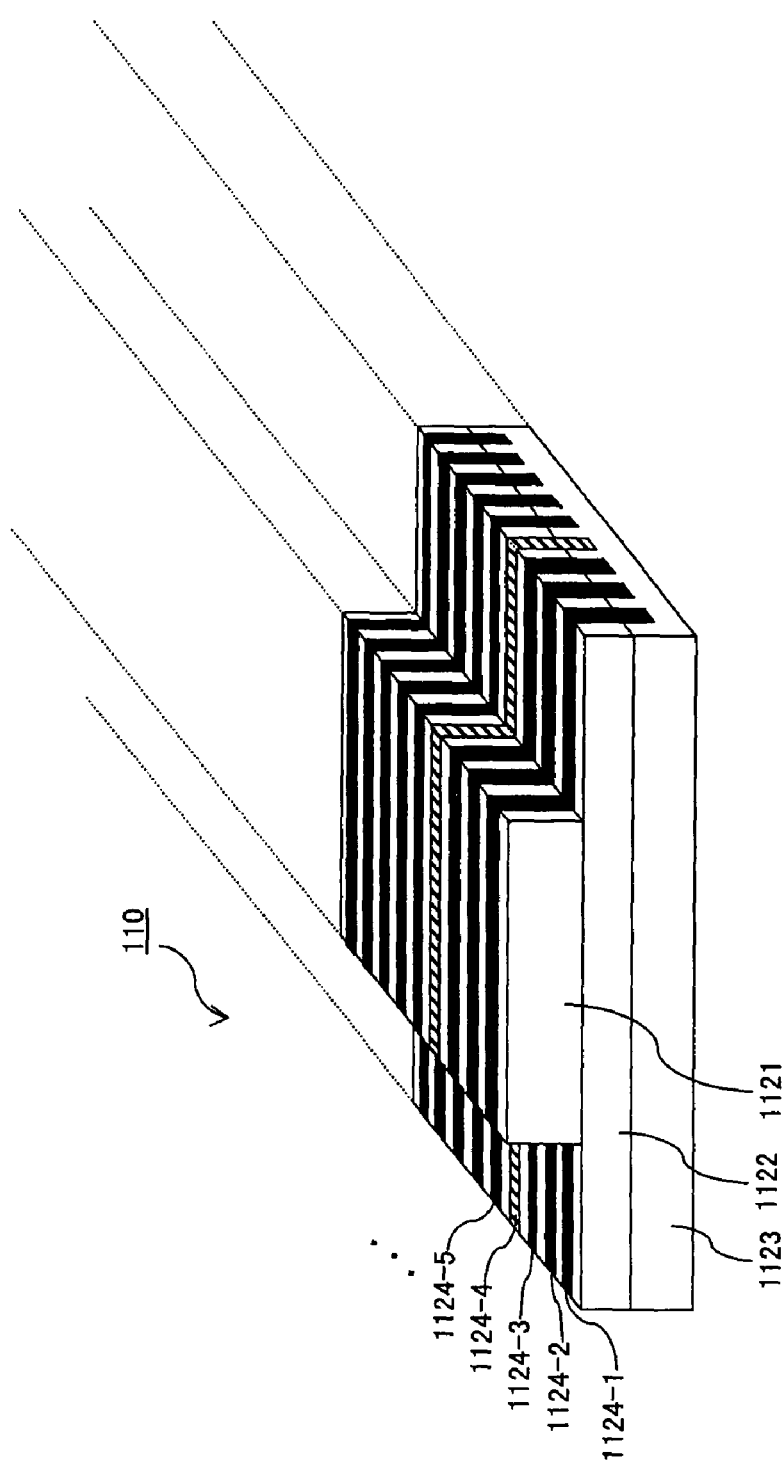
FIG. 19 is a diagram showing an ultrasonic transducer array according to a preferred embodiment of the present invention.

FIG. 19 is a diagram showing an ultrasonic transducer array according to a preferred embodiment of the present invention. Note that the same labels from FIG. 3 are assigned to components that are the same as the comprisal shown in FIG. 3.

Figure 1:
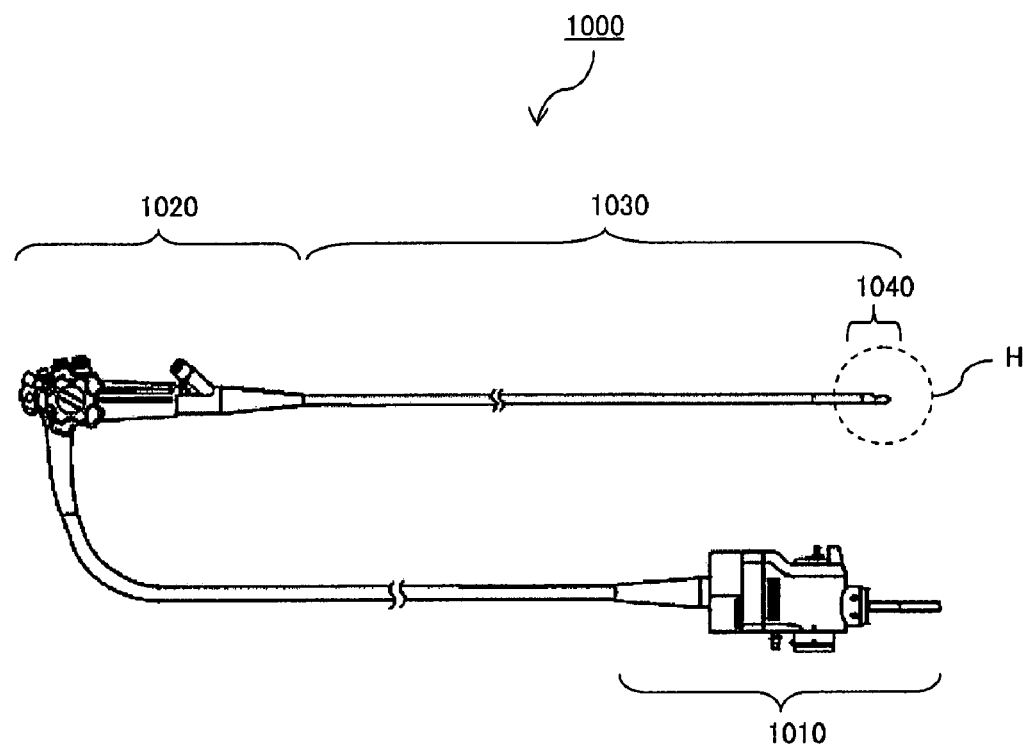
FIG. 1 is a diagram showing a conventional ultrasound endoscope apparatus.
Figure 2:
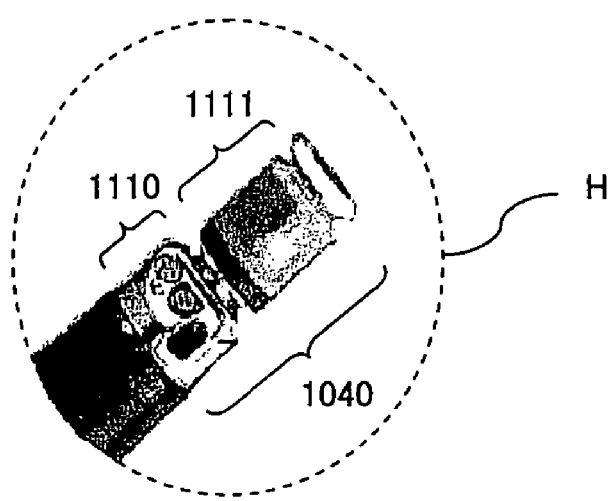
FIG. 2 is an enlarged diagram of the dotted line frame H.
Figure 3:
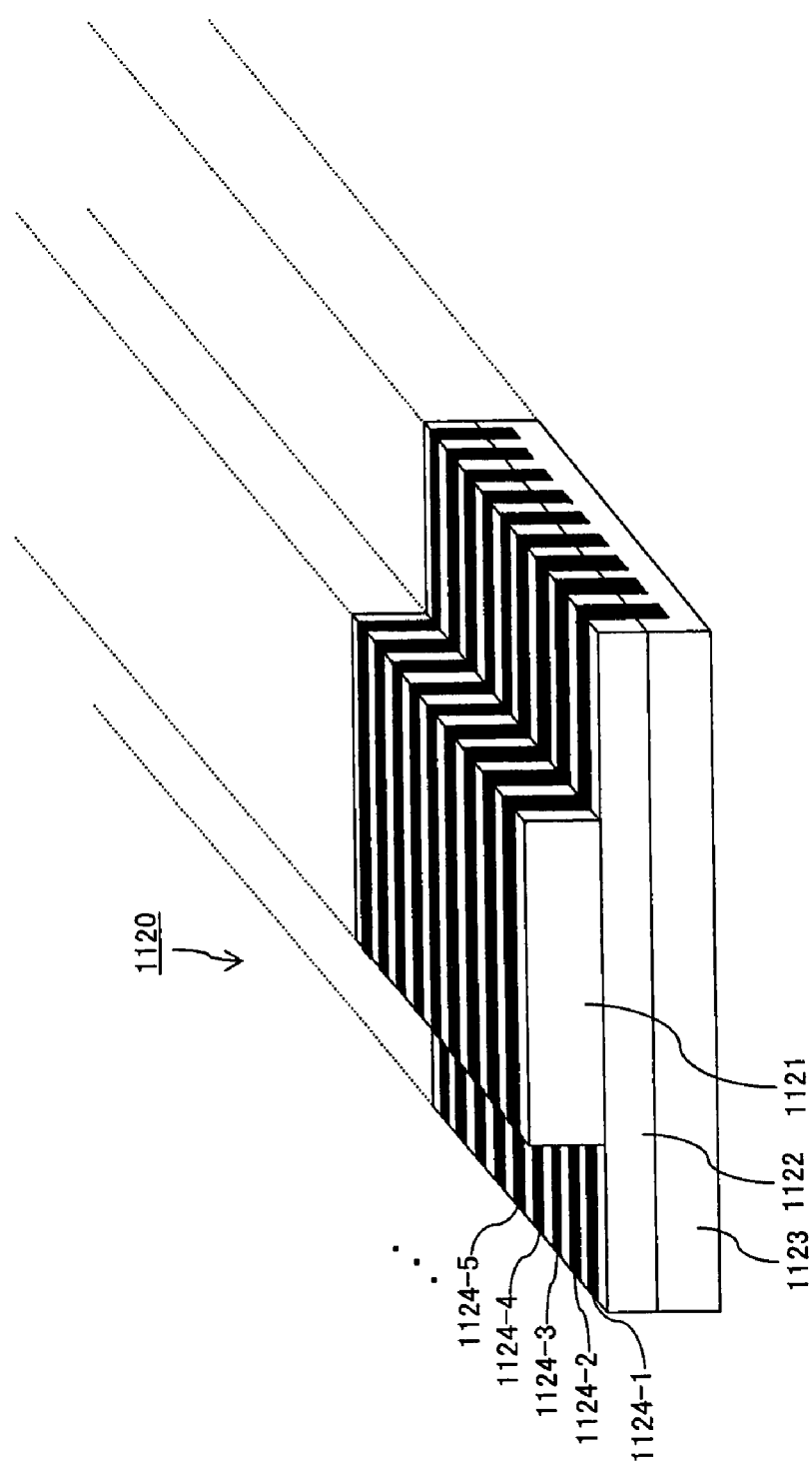
FIG. 3 is a diagram exemplifying an ultrasonic transducer array.
Figure 5:
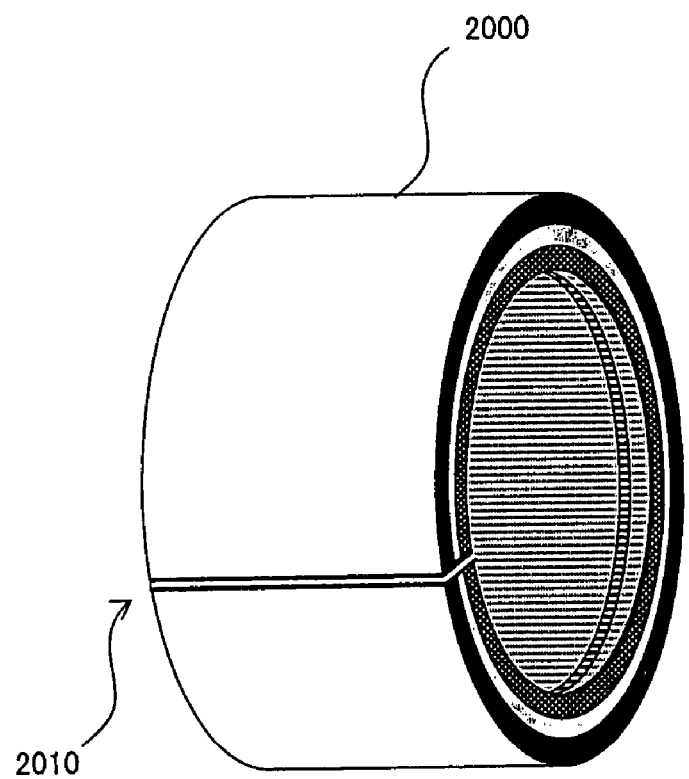
FIG. 5 is a diagram showing a joint part of a common electronic radial type ultrasonic transducer.

For example, the ultrasonic transducer array 110 shown in FIG. 19, comprising a piezoelectric element 1121, a first acoustic matching layer 1122, a second acoustic matching layer 1123 and division members 1124, is equipped in an ultrasound endoscope apparatus in a similar manner to the ultrasonic transducer array 1120 shown in FIG. 3.

The piezoelectric element 1121, first acoustic matching layer 1122 and second acoustic matching layer 1123 are divided into a plurality thereof by commonly formed grooves, thus comprising a plurality of ultrasonic transducers (corresponding to the ultrasonic transducer elements 27).

The division member 1124 is constituted by resin or particles attenuating an ultrasonic wave and is structured by being filled into the grooves commonly formed in the piezoelectric element 1121, first acoustic matching layer 1122 and second acoustic matching layer 1123, followed by being hardened.

Note that the ultrasonic transducer array 110 shown in FIG. 19 is configured to place the piezoelectric element 1121 on two acoustic matching layers, i.e., the first acoustic matching layer 1122 and the second acoustic matching layer 1123; an ultrasonic transducer array 110, however, may also be configured so as to place a piezoelectric element 1121 on one acoustic matching layer or no less than three acoustic matching layers. The ultrasonic transducer array 110 shown in FIG. 19 may also be configured to place a piezoelectric element 1121 on a backing member and form grooves starting from the upper surface of the piezoelectric element 1121 and continuing down to a part of the backing member, thereby constituting a plurality of ultrasonic transducers. The ultrasonic transducer array 110 shown in FIG. 19 may also be configured to place a piezoelectric element 1121 on a backing member, to further place one or more acoustic matching layers on the piezoelectric element 1121, and to form grooves starting from the top surface of the acoustic matching layer and continuing down to a part of the backing member, thereby constituting a plurality of ultrasonic transducers.

The feature of the ultrasonic transducer array 110 shown in FIG. 19 lies in coloring a division member 1124 adjacent to a predefined ultrasonic transducer (i.e., the division member 1124-4 according to the example shown in FIG. 19) by mixing with metallic compounds such as metal powder, colcothar, alumina, tungsten oxide, or silica, or with particles such as carbon, as a colorant for the division member 1124. Note that the division member 1124 may be mixed with a different kinds of colorant. For example, mixing the division member 1124 with colcothar makes it red, mixing the division member 1124 with alumina or silica makes it white, mixing the division member 1124 with tungsten oxide makes it green, and mixing the division member 1124 with carbon makes it black.

Note that the predefined ultrasonic transducer may be an ultrasonic transducer that exists at the end of a plurality thereof that are arrayed continuously and that are capable of transmitting and receiving ultrasonic waves. The predefined ultrasonic transducer may also be, for example, one of two ultrasonic transducers capable of transmitting and receiving two different frequencies, respectively. The predefined ultrasonic transducer may also be one of two ultrasonic transducers having different usage purposes (such as diagnosis and treatment), for example. The predefined ultrasonic transducer may also be one of two ultrasonic transducers existing on the border between the operation part and the non-operation part, for example. That is, referring to FIG. 19, if each ultrasonic transducer adjacent to the division members 1124-1 through 1124-3 is defined as the non-operation part and each ultrasonic transducer adjacent to division members other than the division members 1124-1 through 1124-3 is defined as the operation part, an ultrasonic transducer adjacent to the division member 1124-4 may be defined as a predefined ultrasonic transducer. The color of a division member 1124 adjacent to a predefined ultrasonic transducer may be made to be different from that of other division members 1124 by removing a colorant from the division member 1124 adjacent to the predefined ultrasonic transducer. In addition, two or more of the predefined ultrasonic transducers may be provided in the ultrasonic transducer array 110, and if it is configured as such, then the individual division members 1124 corresponding to those ultrasonic transducers maybe colored differently from one another.

As such, since the color of the division member 1124 adjacent to the predefined ultrasonic transducer is different from that of other division members 1124, it is possible to use the division member 1124 adjacent to the predefined ultrasonic transducer as a positioning mark via a visual or image processing, and therefore this configuration enables the easy identification of the predefined ultrasonic transducer.

This configuration makes it possible to easily identify a predefined ultrasonic transducer that needs to be wired when wiring a signal wire to each ultrasonic transducer in a production process of the ultrasonic transducer array 110.

It is also possible to easily identify a predefined ultrasonic transducer constituting a target of inspection in an inspection of the ultrasonic transducer array 110, for instance.

It is also possible to easily identify a predefined ultrasonic transducer in which a problem has occurred when repairing the ultrasonic transducer array 110, for instance.

The easy identification of a predefined ultrasonic transducer as described above enables the workability and productivity of a worker or technician to be improved and enables an improvement in the prevention of mistakes in the production, inspection, repair, etcetera, of an ultrasound endoscope apparatus.

A change of color on a division member may be for a part thereof, in lieu of being limited to the entirety of the division member.

In the division member 1124-4 shown in FIG. 19 for example, it is possible to change color on only one end part or on only both end parts.

This configuration makes the division members and that of other ultrasonic transducers completely the same for a piezoelectric element 1121 and for other elements close to it, thereby providing the benefit of making the performance of the ultrasonic transducer uniform.

Additionally, it is also possible to use a division member having a different pattern to vary color.

For example, it is possible to have a part for varying a color, for the division member 1124-4 shown in FIG. 19, for example, on only one end part, on only both end parts, or in a plurality of points in the division member; it is also possible to change length of a part of varying a color or to intermingle the place and length of a pattern.

This configuration provides the benefit of enabling a judgment of the significance of points having different colors at a glance by means of a method similar to a barcode.

The ultrasonic transducer array 110 shown in FIG. 19 may also be structured as a radial system ultrasonic transducer array, via end surfaces in the direction perpendicular to the longitudinal direction of the ultrasonic transducer array 110 being connected to each other so as to be formed into a ring shape.

Figure 20:
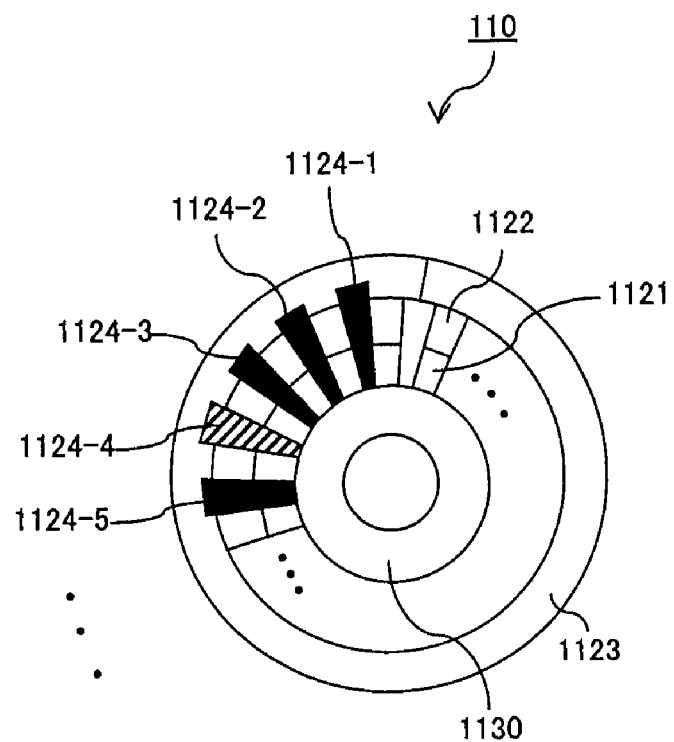
FIG. 20 is a diagram showing a radial system ultrasonic transducer array according to a preferred embodiment of the present invention.

FIG. 20 is a diagram showing a radial system ultrasonic transducer array constituted by the ultrasonic transducer array 110 shown in FIG. 19. Note that the same labels from FIG. 19 are assigned to components that are the same as the comprisal shown in FIG. 19. Note that the ultrasonic transducer array 110 shown in FIG. 20 may be alternatively configured to not comprise a frame member 1130 (corresponding to the structure member 30*a*).

As shown in FIG. 20, even though the ultrasonic transducer array 110 is now structured to be a radial system, making it difficult to discern which ultrasonic transducer is at an end part, a predefined ultrasonic transducer can be easily identified because the color of division member 1124-4 adjacent to the predefined ultrasonic transducer is different from that of other division members 1124-1 and 1124-2.

Defining the ultrasonic transducer at an end part in the operation part as a predefined ultrasonic transducer makes it possible to count ultrasonic transducers in sequence from an ultrasonic transducer at the end part, enabling the easy identification of a target ultrasonic transducer.

FIG. 21 is a diagram showing an ultrasonic transducer array according to another preferred embodiment of the present invention. Note that the same labels from FIG. 19 are assigned to components that are the same as the comprisal shown in FIG. 19.

Similar to the ultrasonic transducer array 110 shown in FIG. 19, the ultrasonic transducer array 130 shown in FIG. 21, comprising a piezoelectric element 1121, a first acoustic matching layer 1122, a second acoustic matching layer 1123, and division members 1124, is equipped in an ultrasound endoscope apparatus.

Note that the ultrasonic transducer array 130 shown in FIG. 21 is configured to place the piezoelectric element 1121 on two acoustic matching layers, i.e., the first acoustic matching layer 1122 and the second acoustic matching layer 1123; however, an ultrasonic transducer array 130 may also be configured to place a piezoelectric element 1121 on one acoustic matching layer or on no less than three acoustic matching layers. The ultrasonic transducer array 130 shown in FIG. 21 may also be configured to place a piezoelectric element 1121 on a backing member and to form grooves starting from the upper surface of the piezoelectric element 1121 and continuing down to a part of the backing member, thereby constituting a plurality of ultrasonic transducers. The ultrasonic transducer array 130 shown in FIG. 21 may also be configured to place a piezoelectric element 1121 on a backing member, to further place one or more acoustic matching layers on the piezoelectric element 1121, and to form grooves starting from the top surface of the acoustic matching layer and continuing down to a part of the backing member, thereby constituting a plurality of ultrasonic transducers.

The feature of the ultrasonic transducer array 130 shown in FIG. 21 lies in the configuration wherein a plate shaped division member 1124 that is colored differently from the division member 1124 adjacent to an ultrasonic transducer other than the predefined ultrasonic transducer is inserted into a groove adjacent to the predefined ultrasonic transducer.

Note that the predefined ultrasonic transducer may be an ultrasonic transducer that exists at the end of a plurality thereof that are arrayed continuously and that are capable of transmitting and receiving ultrasonic waves. The predefined ultrasonic transducer may also be, for example, one of two ultrasonic transducers capable of transmitting and receiving two different frequencies, respectively. The predefined ultrasonic transducer may also be one of two ultrasonic transducers having different usage purposes (such as diagnosis and treatment), for example. The predefined ultrasonic transducer may also be one of two ultrasonic transducers existing on the border between the operation part and the non-operation part for example. That is, referring to FIG. 21, if each ultrasonic transducer adjacent to the division members 1124-1 through 1124-3 is defined as the non-operation part, and each ultrasonic transducer adjacent to division members other than the division members 1124-1 through 1124-3 is defined as the operation part, an ultrasonic transducer adjacent to the division member 1124-4 may be defined as the predefined ultrasonic transducer. In addition, two or more of the predefined ultrasonic transducers may be provided in the ultrasonic transducer array 130, and if it is configured as such, individual division members 1124 corresponding to those ultrasonic transducers may be colored differently from one another. Also, when inserting a plate shaped division member 1124-4 into a groove adjacent to a predefined ultrasonic transducer, a plate shaped division member that is a little larger than the groove may be inserted followed by the removal of a part coming out of the groove.

As such, even if a plate form division member 1124 of a color that is different from that of a division member 1124 adjacent to an ultrasonic transducer other than a predefined ultrasonic transducer is inserted into a groove adjacent to the predefined ultrasonic transducer, it is possible to use the inserted division member 1124 as a positioning mark via visual or image processing, thereby enabling easy identification of the predefined ultrasonic transducer.

The ultrasonic transducer array 130 shown in FIG. 21 may also be structured as a radial system ultrasonic transducer array by end surfaces, locating in the direction perpendicular to the array, of the ultrasonic transducer array 130 being connected to each other so as to be formed into a circular form.

Figure 22:
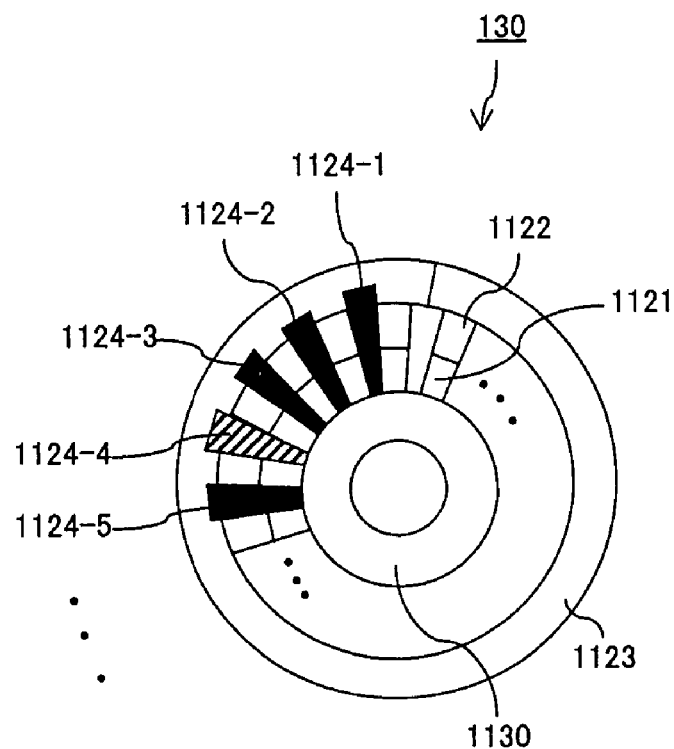
FIG. 22 is a diagram showing a radial system ultrasonic transducer array according to another preferred embodiment of the present invention.

FIG. 22 is a diagram showing a radial system ultrasonic transducer array constituted by the ultrasonic transducer array 130 shown in FIG. 21. Note that the same labels from FIG. 19 are assigned to components that are the same as the comprisal shown in FIG. 19. Note also that the ultrasonic transducer array 130 shown in FIG. 22 may be alternatively configured to not comprise a frame member 1130.

As shown in FIG. 22, even though the ultrasonic transducer array 130 is now structured to be a radial system, making it difficult to discern which ultrasonic transducer is at an end part, a predefined ultrasonic transducer can be easily identified because the color of division member 1124-4 inserted into a groove adjacent to the predefined ultrasonic transducer is different from those of other division members, 1124-1, 1124-2, et cetera.

Defining the ultrasonic transducer at an end part in the operation part as a predefined ultrasonic transducer makes it possible to count ultrasonic transducers in sequence from the one at the end part, enabling the easy identification of a target ultrasonic transducer.

Figure 23:
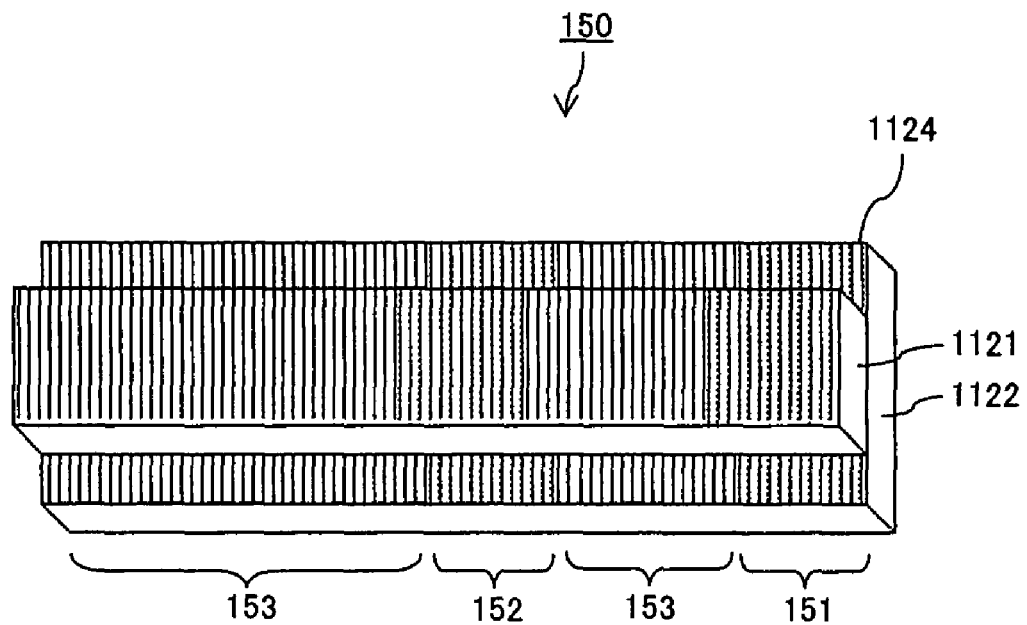
FIG. 23 is a diagram showing an ultrasonic transducer array according to another preferred embodiment of the present invention.

FIG. 23 is a diagram showing an ultrasonic transducer array according to another preferred embodiment of the present invention. Note that the same labels from FIG. 19 are assigned to components that are the same as the comprisal shown in FIG. 19.

The ultrasonic transducer array 150 shown in FIG. 23 comprises a piezoelectric element 1121, a first acoustic matching layer 1122, and division members 1124 that are provided in a common groove for the piezoelectric element 1121 and first acoustic matching layer 1122, constituting a plurality of ultrasonic transducers by virtue of the aforementioned grooves.

In addition, all of the ultrasonic transducers (e.g., 192 ultrasonic transducers thereof) of the ultrasonic transducer array 150 are divided into several blocks, each of which comprises a continuously arrayed plurality of ultrasonic transducers (e.g., 32 ultrasonic transducers thereof) having the same characteristic or function.

In addition, the ultrasonic transducer array 150 differentiates the colors of the division members 1124 for each block.

In the example shown in FIG. 23, all of the ultrasonic transducers are grouped into blocks 151, 152, and 153. Possible methods for grouping the ultrasonic transducers include grouping them according to the difference in frequency of ultrasonic waves, according to usage purposes (i.e., diagnosis, treatment, et cetera), or according to whether they are in the operation part or the non-operation part, among other possibilities.

For example, if block 151 is defined as the non-operation part, block 152 is defined as the group used for treatment, and block 153 is defined as the group used for diagnosis, then the coloring may be such that the division members 1124 placed adjacent to the respective ultrasonic transducers constituting block 151 are colored white, the ones placed adjacent to the respective ultrasonic transducers constituting block 152 are colored red, while the ones placed adjacent to the respective ultrasonic transducers constituting block 153 are colored green.

Note that one possible method for differentiating the color of division members for each block may be by means of filling a groove with a division member 1124 that has been mixed with a specific colorant, then letting the division member 1124 hardened or inserting a plate form division member 1124 that is specifically colored into a groove.

Alternately, the colors may be differentiated of only two division members 1124 placed adjacent to each ultrasonic transducer located on both ends of a certain block from the other division members 1124.

Figure 24:
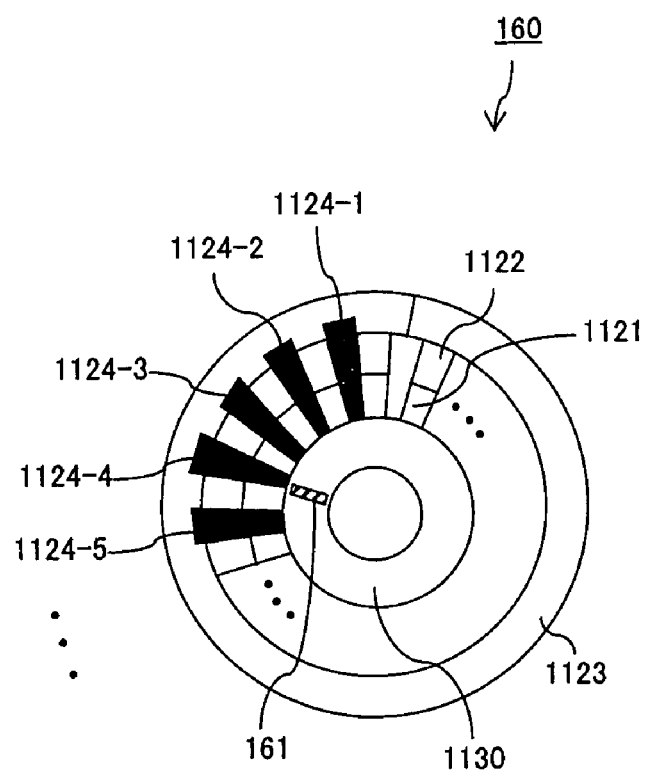
FIG. 24 is a diagram showing a radial system ultrasonic transducer array according to another preferred embodiment of the present invention.

FIG. 24 is a diagram showing an ultrasonic transducer array according to another preferred embodiment of the present invention. Note that the same labels from FIG. 19 are assigned to components that are the same as the comprisal shown in FIG. 19.

The feature of the radial system ultrasonic transducer array 160 shown in FIG. 24 lies in the fact that a mark 161 is attached to a frame member 1130 that is located close to a division member 1124 placed adjacent to a predefined ultrasonic transducer, in order to indicate a position thereof.

Note that the mark 161 may be attached to the frame member 1130 by means of a contact method such as a the use of a marker line, screen printing, or other such method, or a noncontact method such as the use of an inkjet printer, the use of a laser marker, or other such method. Also, the position for attaching a mark 161 to the frame member 1130 may be selected to be close to a predefined ultrasonic transducer. Alternately, the following are possible: a mark 161 may be attached to the frame member 1130 so as to distinguish the characteristic or function of an ultrasonic transducer; a mark 161 may be attached to a prescribed spot on the frame member 1130 in advance for use in assembling the ultrasonic transducer array 160 with the mark 161 being used as a reference point; or, a mark 161 may be attached to a predetermined spot on the frame member 1130 after completing the assembly of the ultrasonic transducer array 160. The color or shape of the mark 161 has no particular limitation.

Thus attaching the mark 161 to the frame member 1130 makes it possible to easily identify a predefined ultrasonic transducer, as in the case of the ultrasonic transducer array 110 and ultrasonic transducer array 130 stated above.

Incidentally, the mark 161 shown in FIG. 24 may be attached at a predetermined spot on a frame member 1130 (i.e., a frame member 1130 placed close to a predefined ultrasonic transducer, or a frame member 1130 placed close to the division member 1124-4) of the ultrasonic transducer array 110 shown in FIG. 20 or the ultrasonic transducer array 130 shown in FIG. 22.

This configuration makes it possible to improve the accuracy of positioning when assembling a plurality of ultrasonic transducers and a frame member 1130 together.

Figure 25:
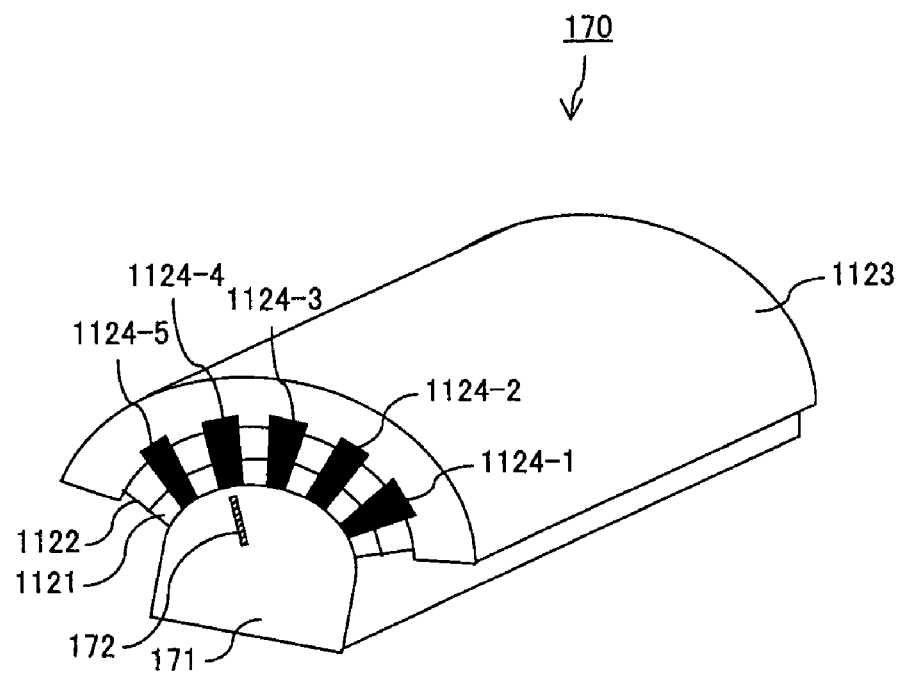
FIG. 25 is a diagram showing a convex system ultrasonic transducer array according to another preferred embodiment of the present invention.

FIG. 25 is a diagram showing an ultrasonic transducer array according to another preferred embodiment of the present invention. Note that the same labels from FIG. 19 are assigned to components that are the same as the comprisal shown in FIG. 19.

The ultrasonic transducer array 170 shown in FIG. 25 is a convex system ultrasonic transducer array transmitting an ultrasonic wave in a radial pattern, and comprises a piezoelectric element 1121; a first acoustic matching layer 1122 and a second acoustic matching layer 1123; division members 1124 equipped in common grooves of the piezoelectric element 1121, first acoustic matching layer 1122, and second acoustic matching layer 1123; and a frame member 171 for retaining a plurality of ultrasonic transducers divisionally structured as a result of the aforementioned grooves dividing the piezoelectric element 1121, first acoustic matching layer 1122, and second acoustic matching layer 1123.

The feature of the convex system ultrasonic transducer array 170 shown in FIG. 24 lies in the fact that a mark 172 is attached to a frame member 171 placed close to a division member 1124-4 existing close to a predefined ultrasonic transducer, in order to indicate the position thereof.

Note that the mark 172 may be attached to the frame member 171 by means of a contact method such as the use of a marker line, screen printing, or other such method, or a non-contact method such as the use of an inkjet printer, the use of a laser marker, or other such method. Also, the position for attaching a mark 161 to the frame member 171 may be close to a predefined ultrasonic transducer. Alternately, the following are possible: a mark 172 may be attached to the frame member 171 so as to distinguish the characteristic or function of an ultrasonic transducer; a mark 172 may be attached to a prescribed spot on the frame member 171 in advance for use in assembling the ultrasonic transducer array 170, with the mark 172 being used as a reference point; or, a mark 172 may be attached to a predetermined spot of the frame member 171 after completing the assembly of the ultrasonic transducer array 170. The color or the shape of the mark 172 has no particular limitation.

Thus attaching the mark 172 to the frame member 171 makes it possible to easily identify a predefined ultrasonic transducer, as in the case of ultrasonic transducer array 110 and ultrasonic transducer array 130.

Figure 26:
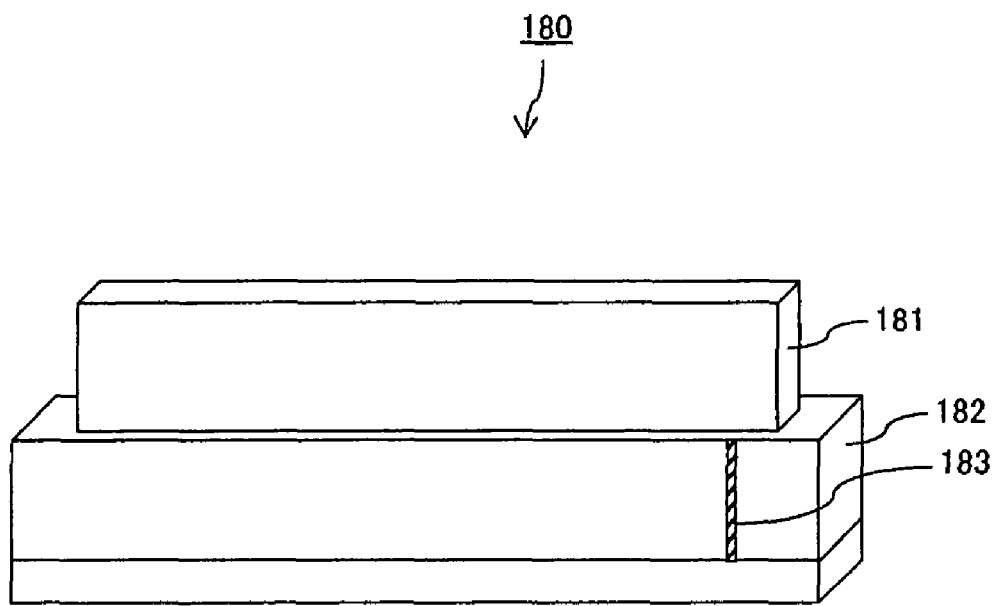
FIG. 26 is a diagram showing a linear system ultrasonic transducer array according to another preferred embodiment of the present invention.

FIG. 26 is a diagram showing an ultrasonic transducer array according to another preferred embodiment of the present invention. Note that the same labels from FIG. 19 are assigned to components that are the same as the comprisal shown in FIG. 19.

The ultrasonic transducer array 180 shown in FIG. 26, which is a linear system ultrasonic transducer array for transmitting an ultrasonic wave in a straight line, comprises an ultrasonic transducer part 181 constituted by a plurality of ultrasonic transducers arrayed in a straight line, an acoustic matching layer and division members, and a frame member 182 for retaining the plurality of ultrasonic transducers.

The feature of the linear system ultrasonic transducer array 180 lies in the fact that a mark 183 is attached to a frame member 182 placed close to a division member existing adjacent to a predefined ultrasonic transducer, in order to indicate the position thereof.

Note that the mark 183 maybe attached to the frame member 182 by means of a contact method such as the use of a marker line, screen printing, or other such methods, or a noncontact method such as the use of an inkjet printer, the use of a laser marker, or other such methods. Also, the position for attaching a mark 183 to the frame member 182 may be close to a predefined ultrasonic transducer. Alternately, the following are possible: a mark 183 may be attached to the frame member 182 so as to distinguish the characteristic or function of an ultrasonic transducer; a mark 183 may be attached to a prescribed spot of the frame member182 in advance for use in assembling the ultrasonic transducer array 180, with the mark 183 being used as a reference point; or a mark 183 may be attached to a predetermined spot of the frame member 182 after completing the assembly of the ultrasonic transducer array 170. The color or shape of the mark 183 is not particularly limited.

Thus attaching the mark 183 to the frame member 182 makes it possible to easily identify a predefined ultrasonic transducer, as in the case of the ultrasonic transducer array 110 and ultrasonic transducer array 130.

FIG. 27 is a diagram showing an ultrasonic transducer array according to another preferred embodiment of the present invention. Note that the same labels from FIG. 19 are assigned to components that are the same as the comprisal shown in FIG. 19.

The feature of the radial system ultrasonic transducer array 190 shown in FIG. 27 lies in the fact that individual ultrasonic transducers is formed into a circular pattern by connecting, via a connection member 191, the end faces in the direction perpendicular to the longitudinal direction of the ultrasonic transducer array 110 shown in FIG. 19, and also the fact that the color of the connection member 191 is different from that of the division members 1124. Note that the material of the connection member 191 is not limited to any particular material.

As such, even if the ultrasonic transducer array 190 is a radial system ultrasonic transducer array, the differentiation of the color of the connection member 191 from that of division members 1124 makes it possible to identify an ultrasonic transducer at an end part and therefore the ultrasonic transducer can be counted in sequence from the one at the end part, thereby enabling the easy identification of a predefined ultrasonic transducer.

Figure 28:
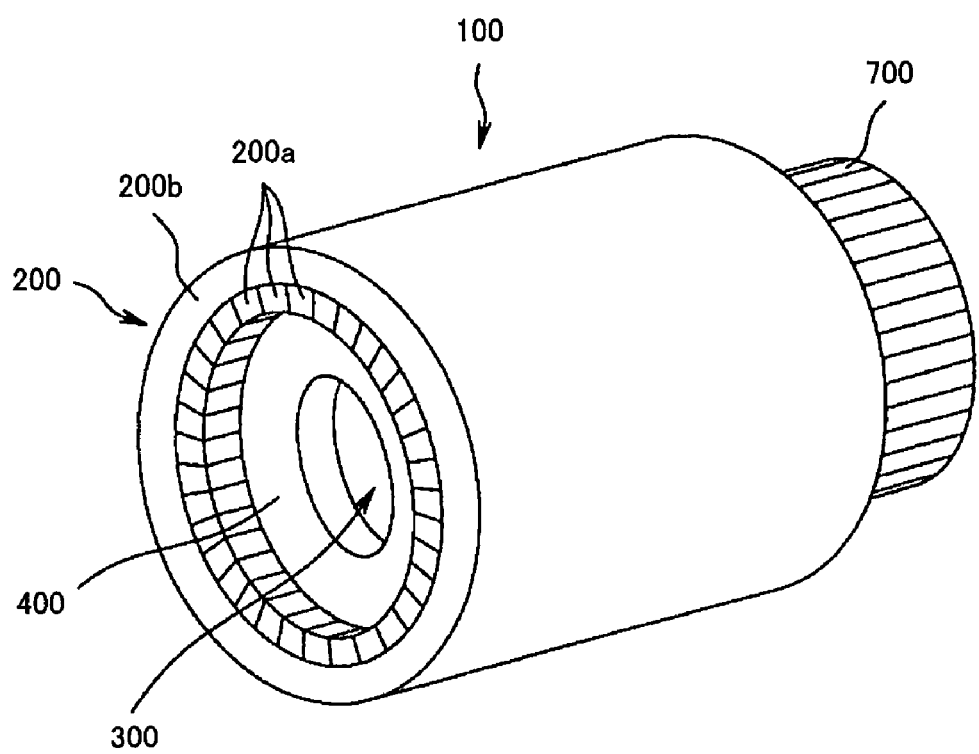
FIG. 28 is a diagonal view diagram of an ultrasonic transducer.

FIG. 28 is a diagonal view diagram of an ultrasonic transducer.

The ultrasonic transducer 100 according to the present embodiment as shown in FIG. 28, being configured as a radial array type, primarily comprises an acoustic matching layer 200, a piezoelectric element (to be described later), a backing member 300 and an transducer shape forming member 400 (corresponding to the structure member 30a or frame member 1130), which is formed into a cylindrical shape.

The acoustic matching layer 200 is formed by layering the first acoustic matching layer 200a, which is hardened by using materials including a plastics member (such as epoxy series, silicone series, polyimide series, et cetera) mixed with powder or fibers (such as metal, ceramics, glass, et cetera), or materials including glass, machinable ceramics, silicon, or other such materials, and the second flexible acoustic matching layer 200b, which is made of a resin member (such as silicone, epoxy, PEEK (Registered Trademark), polyimide, polyether imide, polysulfone, polyether sulfone, fluorine series resin, et cetera), or an elastomer-like material. A board 700 is described later herein.

The transducer shape forming member 400 is formed by a fiber-reinforced thermoset polyphenylether (PPE). The fiber-reinforced thermosetting PPE has characteristics such as high shape accuracy and insulation properties, allowing the attachment of a conductor pattern, thermal resistance against soldering, and a high adhesiveness. Preferably usable brand names include "TLC-W-596" and "TLC-W-598" manufactured by KYOCERA Chemical Corp.; "PPC series", "RCC series" and "A PPE series" manufactured by Asahi Kasei Corp.; and "CS-3376 series" and "CS-3665E series" manufactured by Risho Kogyo Co., Ltd., for example.

Figure 30:
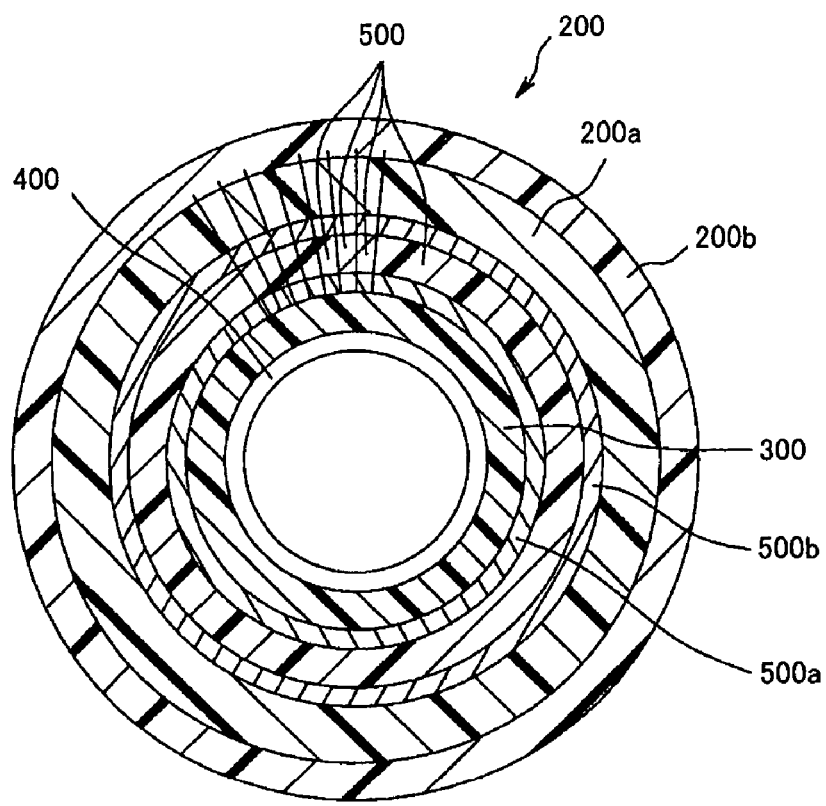
FIG. 30 is a cross-sectional diagram of the section A-A shown in FIG. 29.

FIG. 29 is a longitudinal cross-sectional diagram describing a comprisal of an ultrasonic transducer; FIG. 30 is a cross-sectional diagram of the section A-A shown in FIG. 29.

As shown in FIGS. 29 and 30, the ultrasonic transducer 100 comprises, in order from the center side, a backing member 300, piezoelectric element 500 and board 700, a first acoustic matching layer 200a and a second acoustic matching layer 200b.

As shown in FIGS. 28 and 30, the backing member 300 and the first acoustic matching layer 200a are arrayed by being divided into predetermined pieces, respectively, e.g., 192 pieces. The internal periphery side of each piezoelectric element 500 is equipped with one-face-side electrode 500a and the outer periphery side is equipped with an other-face-side electrode 500b.

Figure 31:
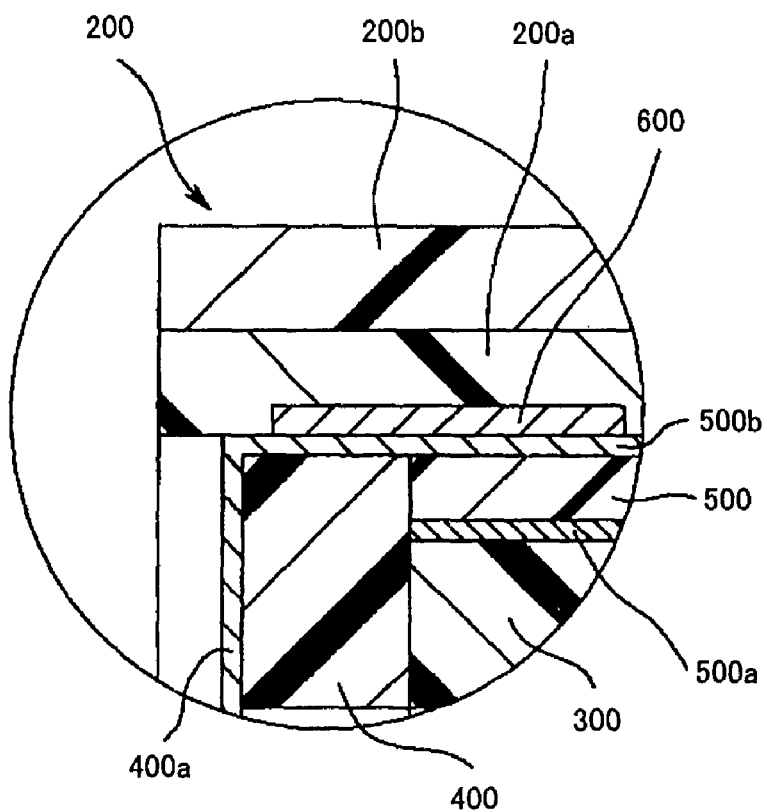
FIG. 31 is an enlarged diagram of the part indicated by arrow B in FIG. 29.
Figure 32:
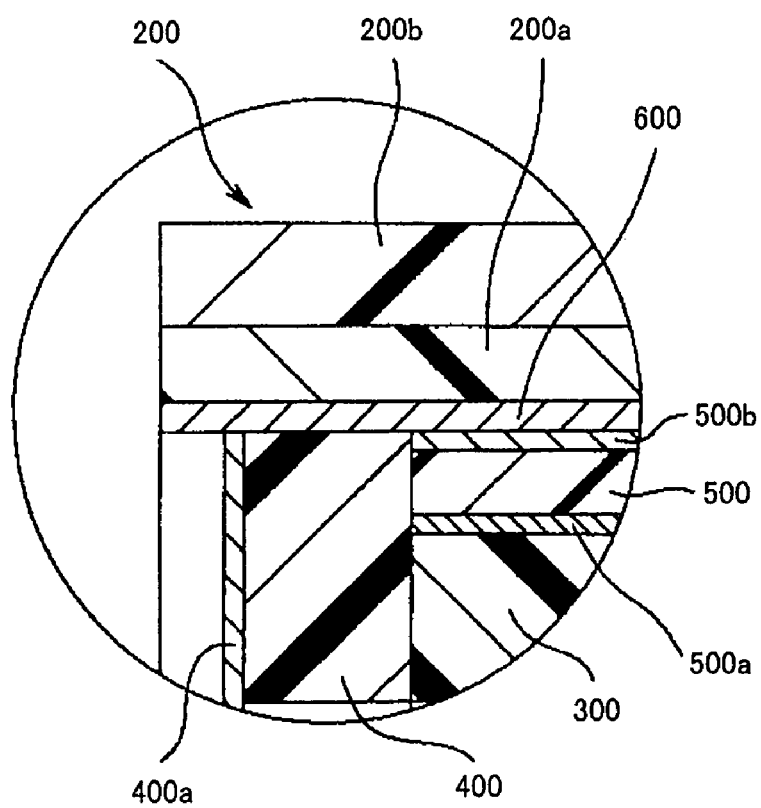
FIG. 32 is a diagram describing another configuration example of the part indicated by arrow B in FIG. 29.

FIG. 31 is an enlarged diagram of the part indicated by arrow B in FIG. 29; FIG. 32 is a diagram describing another configuration example of the part indicated by arrow B in FIG. 29; FIG. 33 is a diagram describing another configuration example of the part indicated by arrow B in FIG. 29; and FIG. 34 is an enlarged diagram of the part indicated by arrow C in FIG. 29.

As shown in FIGS. 31 and 32, one end side of the ultrasonic transducer 100 comprises the acoustic matching layer 200 and is comprised so as to protrude further than the piezoelectric element 500. In addition, the transducer shape forming member 400 is fixed, with an adhesive, on the internal circumferential surface of the first acoustic matching layer 200a constituting the protruding acoustic matching layer 200.

A predetermined position of the first acoustic matching layer 200a constituting the acoustic matching layer 200 is equipped with a ground-use conductive material ("ground electrode" hereinafter) 600 that is configured to place a band-formed conductive material in such a way so as to be approximately flush with the surface of the first acoustic matching layer 200a, for example. Electrical continuity is obtained for the other-face-side electrode 500b to the ground electrode 600 by placing the other-face-side electrode 500b thereon.

In addition, the present embodiment is configured to equip a conduction part 400a on one-face-side and on a face, that is a predetermined position of the transducer shape forming member 400, opposite the ground electrode 600 on the outer circumferential surface. Electrical continuity is obtained for the conduction part 400a to the ground electrode 600 by fixing, with a conductive adhesive (not shown herein) that is a conductive member, the transducer shape forming member 400 on the internal circumferential surface of the first acoustic matching layer 200a. The conductive member may be soldering, metallic grazing such as silver grazing, gold grazing, et cetera, or a conductive film, instead of being limited to being a conductive adhesive.

Also, the conduction part 400a may be equipped only on one-face-side of the transducer shape forming member 400, as shown in FIG. 33. In such a case, the configuration is such that the ground electrode 600 is externally exposed and electrical continuity for the conduction part 400a to the ground electrode 600 is secured by using a conductive material such as a conductive resin, conductive painting, or other such material, or a conductive film such as one of various conductive thin films, a thick film, plating, et cetera. Also possible is a combination of the aforementioned means.

As shown in FIG. 34, a board 700 that is formed into approximately the same thickness as the piezoelectric element 500 is placed adjacent to the other end side of the ultrasonic transducer 100. The board 700 is a three-dimensional board, alumina board, glass epoxy board, rigid flexible board, flexible board, or other such board, in which a conductive pattern 700a formed on the board 700 is electrically connected to the one-face-side electrode 500a of the piezoelectric element 500 by way of a conduction member 800 placed on the conductive pattern 700a and the face-side electrode 500a.

Note that the piezoelectric element 500 is formed by cutting a plate-formed piezoelectric ceramics such as lead zirconate titanate, lead titanate, barium titanate, or BNT-BS-ST, or piezoelectric crystallization (such as $LiNbO_3$ or PZNT) and relax or ferroelectrics one-side electrode 500a and the other-face-side electrode 500b each is configured, in advance, in such a manner that a conductive member such as gold, silver, copper, nickel, or chromium is placed, in a form of thin film by baking, vapor deposition, sputtering, or ion plating, or by plating the above materials as a single layer, multiple layers or an alloy layer onto the surface of a plate-formed piezoelectric ceramic.

The backing member 300 may be made of various materials such as a resin member (such as epoxy, silicone, polyimide, polyether imide, polyetherether ketone (PEEK), urethane, or fluorine), an elastomer material (such as a chloroprene elastomer, propylene series elastomer, butadiene series elastomer, urethane series elastomer, silicone series elastomer, or fluorine series elastomer), or these resin materials or elastomer materials mixed with the filler of a single material or a plurality of materials and/or forms consisting of powder, fiber or hollow particles constituted by a metal such as tungsten, ceramics (such as alumina, zirconia, silica, tungsten oxide, piezoelectric ceramic powder, or ferrite), glass, resin, or other such materials. The present embodiment is configured to use an epoxy resin mixed with alumina powder followed by hardening of the mixture.

Next is a description of an assembly process of the ultrasonic transducer 100 configured as described above by referring to FIGS. 35 through 47.

(1) Process for Forming the Acoustic Matching Layer 200

FIG. 35 is a diagram describing members for forming an acoustic matching layer, and FIG. 36 is a diagram describing the acoustic matching layer.

In order to form the acoustic matching layer 200, in the first step the first acoustic matching layer 200a and second acoustic matching layer 200b are prepared. These acoustic matching layers have predetermined sizes and forms, as shown in FIG. 35, and the acoustic impedance values are adjusted to predetermined values. A plate shaped ground electrode 600 is placed on a prescribed position of the one-face-side of the first acoustic matching layer 200a.

Next the acoustic matching layer 200 is formed by integrally layering the first acoustic matching layer 200a and the second acoustic matching layer 200b, as shown in FIG. 36. In this process, the second acoustic matching layer 200b is placed on the other-face-side of the first acoustic matching layer 200a where a ground electrode 600 is not provided. As described in the present embodiment, the acoustic matching layers may be integrated after each thereof is made to be predetermined thickness; the predetermined thickness of the acoustic matching layers may be established after the integration, the layers may be formed directly by the coating, injection molding, filming, or other such methods of one layer to the other in place of joining the two layers with an adhesive, or the above described methods may be combined.

The ground electrode can be constituted by adhering a conductive member 1200 formed as a plate of predetermined width and thickness to a groove 1100 of predetermined width and depth that was formed at a predetermined position on the first acoustic matching layer 200a; by adhering in the groove 1100 a conductive member 1200 formed as a plate of predetermined width and a thickness that is a little thicker than the aforementioned depth or by filling (or coating) the groove 1100 with a conductive resin or other such material so as to cause it to protrude from the groove followed by processing to make the protruded conductive member flush with the surface of the first acoustic matching layer 200a; by adhering a conductive member into the groove 1100 (or filling the groove 1100 with a conductive member or coating the groove 1100 with a conductive member) of the first acoustic matching layer 200a that formed to be thicker than a predetermined thickness followed by processing to make it the predetermined thickness; or by one of various conductive films. Note that the ground electrode 600 can use a conductive material such as a conductive resin, conductive paint, metal, et cetera, and a conductive film such as one of various conductive thin films, a conductive thick film, plating, et cetera.

(2) Process for Forming a First Layer Body

Figure 37:
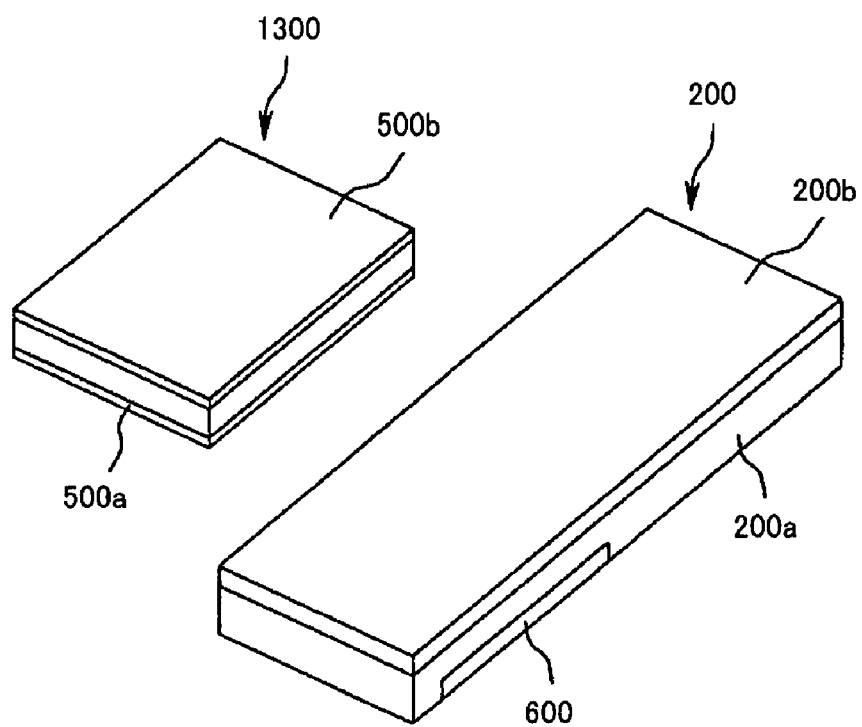
FIG. 37 is a diagram describing members for forming a first layer body.

FIG. 37 is a diagram describing a member for forming a first layer body, and FIG. 38 is a diagram describing the first layer body.

In order to form the first layer body, the acoustic matching layer 200 is prepared in the first step, and piezoelectric ceramics 1300 are provided with the one-face-side electrode 500a and other-face-side electrode 500b as shown in FIG. 37. The piezoelectric ceramics 1300 are formed to be shorter than the length of the acoustic matching layer 200 by a predetermined size, to be approximately the same width and to be a predetermined thickness.

Next, the acoustic matching layer 200 is turned over, as shown in FIG. 38, the other-face-side electrode 500b of the piezoelectric ceramics 1300 is placed at a prescribed position on the ground electrode 600 provided on the first acoustic matching layer 200a, in which state is fixed onto the first acoustic matching layer 200a (with an adhesive, not shown herein) the piezoelectric ceramics 1300.

This process forms the first layer body 2100, integrating the acoustic matching layer 200 and piezoelectric ceramics 1300 and giving them electrical continuity between the other-face-side electrode 500b and the ground electrode 600. In this event, one of the end face sides of the acoustic matching layer 200 equipped with the ground electrode 600 is in the state of protruding from one of the end surface sides of the piezoelectric ceramics 1300 by a prescribed amount "a".

(3) Process for Forming a Second Layer Body

Figure 39:
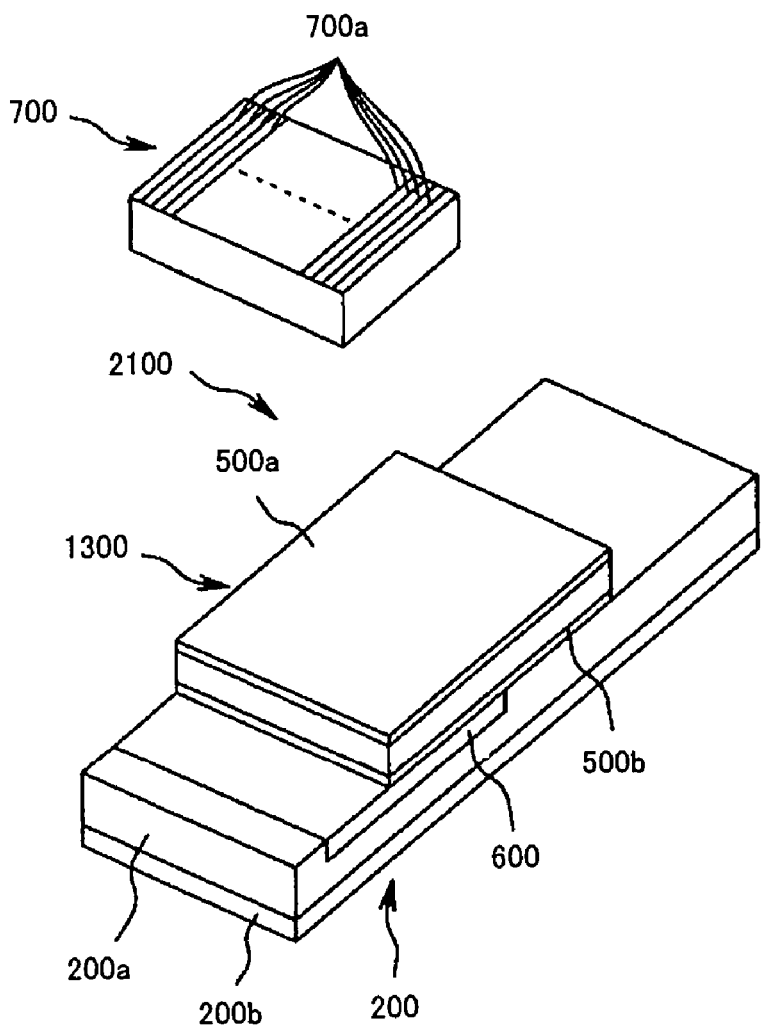
FIG. 39 is a diagram describing members for forming a second layer body.
Figure 40:
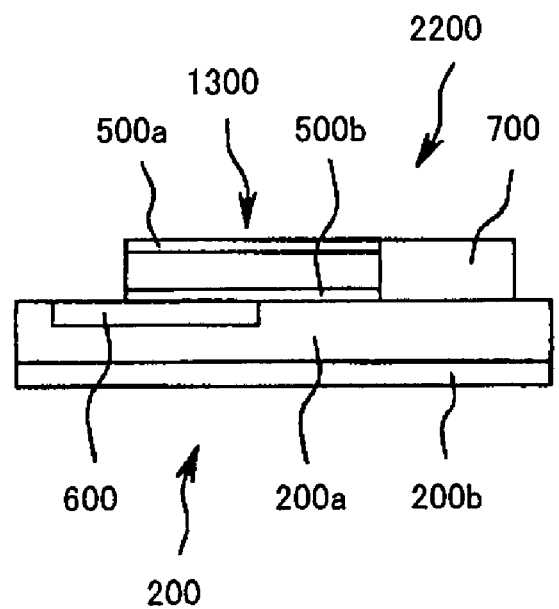
FIG. 40 is a diagram describing the second layer body.

FIG. 39 is a diagram describing members for forming a second layer body, and FIG. 40 is a diagram describing the second layer body.

In order to form the second layer body, in the first step are prepared the first layer body 2100 and a board 700 that is approximately the same thickness as the piezoelectric ceramics 1300 shown in FIG. 39 and that can have a regularly formed plurality of conductive pattern 700a on one surface. Next, the board 700 is placed next to the piezoelectric ceramics 1300 in the state of the conductive pattern 700a being upside as shown in FIG. 40, and is adhered onto the first acoustic matching layer 200a.

This process forms the second layer body 2200, with the piezoelectric ceramics 1300 and board 700 being placed adjacent to each other on the surface of the first acoustic matching layer 200a. Note that the width and length of the board 700 are set at the respective predetermined sizes.

(4) Process for Electrically Connecting the Conductive Pattern 700a to the One-Face-Side Electrode 500a of the Piezoelectric Ceramics 1300

Figure 41:
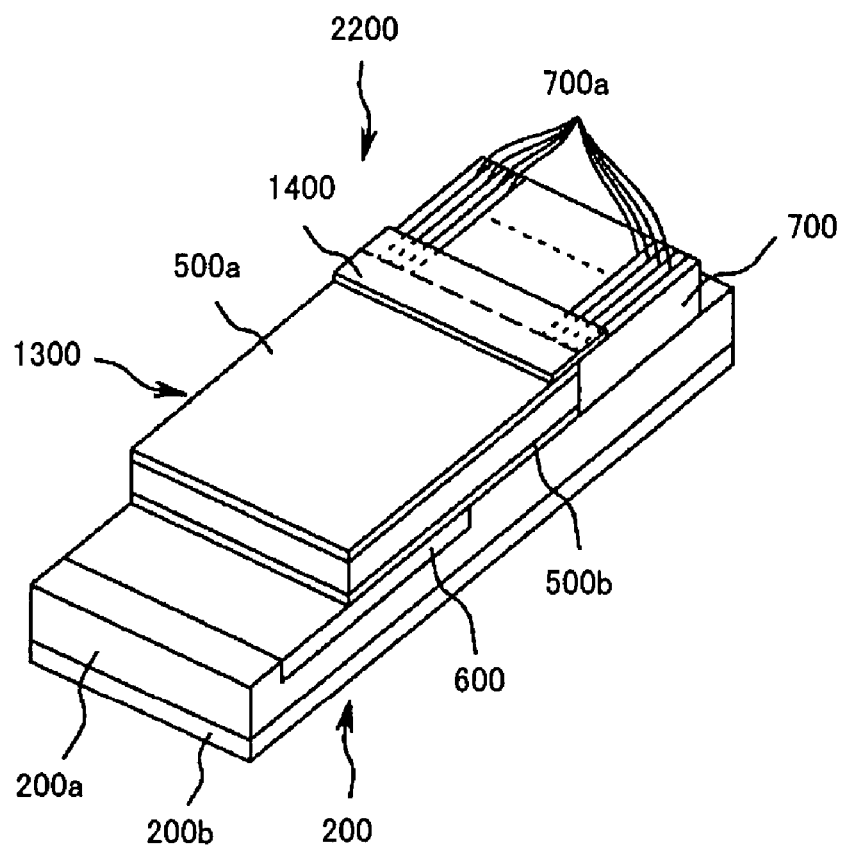
FIG. 41 is a diagram describing a process for electrically connecting a face-side electrode of a piezoelectric ceramics to the conduction pattern of a board.

FIG. 41 is a diagram describing a process for electrically connecting a one-face-side electrode of piezoelectric ceramics to the conduction pattern of a board.

As shown in FIG. 41, in the first step a mask member (not shown herein) is placed at a predetermined position on the surfaces of the board 700, which has the conductive pattern 700a, and on the surface of the piezoelectric ceramics 1300, which have the one-face-side electrode 500a, of the second layer body 2200, and a conductive paint or conductive adhesive is coated on them son that a conductive film part 1400 is formed on them.

This process electrically connects the conductive pattern 700a to the one-face-side electrode 500a by way of the conductive film part 1400.

(5) Process for Dividing the Piezoelectric Ceramics 1300 into a Plurality of Piezoelectric Elements 500

Figure 43:
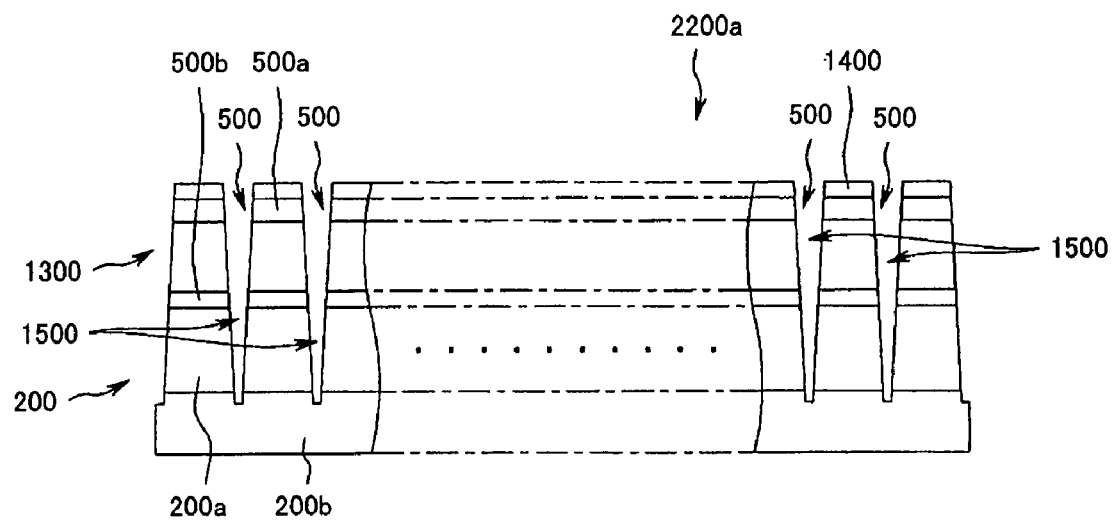
FIG. 43 is a diagram showing a second layer body with a predetermined number of division grooves.

FIG. 42 is a diagram showing a state of dividing piezoelectric ceramics into piezoelectric elements via division grooves, FIG. 43 is a diagram showing a second layer body that has a predetermined number of division grooves, and FIG. 44 is a diagram showing the deformation of a second layer body that has a plurality of piezoelectric elements.

As shown in FIG. 42, there are division grooves 1500 of a predetermined depth starting from the surface of the piezoelectric ceramics 1300 and the board 700, cutting through the first acoustic matching layer 200a constituting the acoustic matching layer 200, and reaching a part of the second acoustic matching layer 200b; these are made a predetermined width or predetermined form in a predetermined pitch in the direction perpendicular to the longitudinal direction by using cutting means such as a dicing saw or laser apparatus (neither is shown herein). To do this, the cutting means is placed on the center line that divides the two conductive patterns 700a.

This process divides the board 700 that has a plurality of conduction patterns 700a into a plurality of boards 700 that have the conductive pattern 700a and also divides one piece of the piezoelectric ceramics 1300 into a plurality of piezoelectric elements 500 (corresponding to the above described ultrasonic transducer elements 27 or to a plurality of ultrasonic transducers). In this event, the conductive film part 1400 is also divided into a plurality of conductive members 800. This process arrays the piezoelectric elements 500 to which the conductive pattern 700a is connected by way of the conductive members 800 on the acoustic matching layer 200.

By the forming of a predetermined number of the division grooves 1500 in the second layer body 2200 at a predetermined pitch as shown in FIG. 43, the piezoelectric ceramics 1300, the board 700, the conductive film part 1400 and the first acoustic matching layer 200a are divided into a predetermined number of pieces, and thus changing the second layer body 2200 comprised a piezoelectric ceramics 1300 and a board 700 into a second layer body 2200a equipped with a plurality of piezoelectric elements 500 and boards 700. That is, causing a plurality of piezoelectric elements 500 to be arrayed on the second acoustic matching layer 200b having flexibility and constituting the acoustic matching layer 200.

Therefore, the second layer body 2200a comprising a plurality of piezoelectric elements 500 can be formed into a cylindrical form as shown in FIG. 44 by bending the second layer body 2200 with placing the second acoustic matching layer 200b on the outermost circumference.

Note that a part that becomes unnecessary for the formation of the ultrasonic transducer 100, for example the part of the acoustic matching layer 200 indicated by the diagonal lines in FIG. 42, is removed after forming the division grooves 1500. Likewise, unnecessary parts can eventually be removed by using larger sizes of individual members constituting the second layer body (greater length for example) than the predetermined forms. Furthermore, an electrical continuity test is carried out, on an as-required basis, to validate the electrical connection of the one-face-side electrode 500*a* of each of the piezoelectric elements 500 to the conductive pattern 700*a* of the board 700 by way of the conductive member 800.

(6) Process for Forming a Cylindrical Unit 2300

FIG. 45 is a diagram describing a member for forming a cylindrically formed transducer unit, FIG. 46 is a diagram showing the placement of an transducer shape forming member on the first acoustic matching layer, and FIG. 47 is a diagram showing the placement of the transducer shape forming member on a board.

In order to form a cylindrical unit 2300, in the first step are prepared the second layer body 2200*a* and the cylindrically formed transducer shape forming members 400A and 400B that are respectively formed into predetermined sizes by using fiber reinforced thermosetting PPE members, as shown in FIG. 45. Next, the second layer body 2200*a* is formed into a cylinder followed by the integral fixing, with a conductive adhesive, of the transducer shape forming member 400A onto the first acoustic matching layer 200*a* of the acoustic matching layer 200, as shown in FIG. 46.

Also, the transducer shape forming member 400B is integrally fixed with a nonconductive adhesive onto the internal circumference side of the board 700 provided adjacent to the piezoelectric elements 500, as shown in FIG. 47.

This process adherently fixes the first acoustic matching layer 200*a*, which is a hard member, to the transducer shape forming member 400A, which is made of a fiber reinforced thermosetting PPE, and fixes a board 700 to the transducer shape forming member 400B, which is also a fiber reinforced thermosetting PPE, hence forming the cylindrical unit 2300 having a prescribed curvature from the second layer body 2200*a*. In this event, the ground electrode 600, which has an electrical continuity with the other-face-side electrodes 500*b* provided on each of the divided piezoelectric elements 500, and the conduction part 400*a* of the transducer shape forming member 400A come to have an integral electrical continuity. The connection of a ground wire extending from an ultrasonic wave observation apparatus (not shown herein) to the conduction part 400*a* secures a ground connection with a sufficiently large capacity. Note that the transducer shape forming member 400A may alternatively be fixed with a nonconductive adhesive, followed by electrically connecting it by means of a conductive thin film, conductive resin, conductive thick film, or other such conductor, without ushering in any problems.

The backing member uses a material such as an elastomer mixed with ferrite or epoxy resin mixed with alumina powder for the one-face-side electrode 500*a* side, and is added by means of an adhesion, injection molding, or other such process. This process forms a radial array type ultrasonic transducer comprised as shown in the above described FIGS. 28 through 30.

Figure 49:
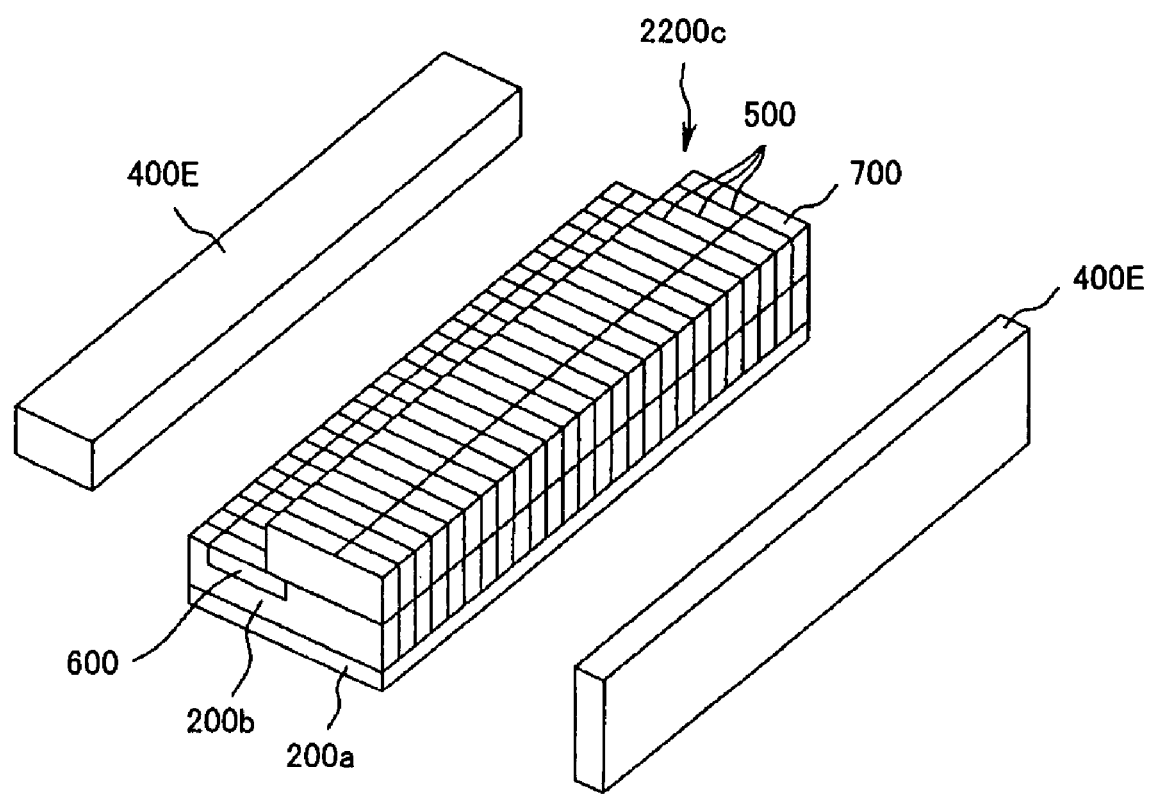
FIG. 49 is a diagram showing an transducer shape forming member and a second layer body used for forming a linear array type transducer unit.

FIG. 48 is a diagram showing an transducer shape forming member and a second layer body for forming a convex array type transducer unit, and FIG. 49 is a diagram showing an transducer shape forming member and a second layer body for forming a linear array type transducer unit.

As described above, the present embodiment is a process for forming the radial array type ultrasonic transducer 100 using the transducer shape forming members 400A and 400B, whereas a convex array type transducer unit is formed by fixing, in lieu of using the transducer shape forming members 400A and 400B which have been shown in the process for forming the cylindrical unit 2300 described in the above paragraph (6), transducer shape forming members 400C and 400D, which are respectively formed into a partial circle as shown in FIG. 48, onto a first acoustic matching layer 200*a* of a second layer body 2200*b*, which is divided into a predetermined number of pieces in a prescribed form as described above, comprising piezoelectric elements 500.

Comparably, a linear array type ultrasonic transducer is formed by fixing a plate-formed transducer shape forming member 400E, of which the end part is flat, onto a first acoustic matching layer 200*a* of a second layer body 2200*c* in such a manner that the flat part comes to contact with the first acoustic matching layer 200*a*, as in the above description and as shown in FIG. 49. Furthermore, an end part form of the transducer shape forming member is not limited to being circular or linear, and instead a combination or modification of those shapes is viable, thereby making it possible to set an ultrasonic wave scanning direction discretionarily.

As described above, the fixed placement of an transducer shape forming member made of a fiber-reinforced thermosetting PPE formed into a prescribed form onto a hard first acoustic matching layer constituting an acoustic matching layer and protruding from the piezoelectric elements makes it possible to highly accurately form an ultrasonic transducer in a prescribed form and also to form the ultrasonic transducer while preventing, with certainty, the occurrence of a failure due to residual stress.

With this fixed placement of an transducer shape forming member, piezoelectric elements formed by dividing piezoelectric ceramics into a plurality of pieces are arrayed highly accurately, thereby enabling the obtainment of ultrasonic wave observation images of high image quality over a long period of time.

Note that the above described embodiments are configured to use a fiber-reinforced thermosetting PPE for the transducer shape forming member; they may, however, use a common hard member for the transducer shape forming member, over which an insulative member made of a fiber-reinforced thermosetting PPE in the same form may be used as the transducer shape forming member as a member for insulating the ultrasonic transducer.

Figure 50:
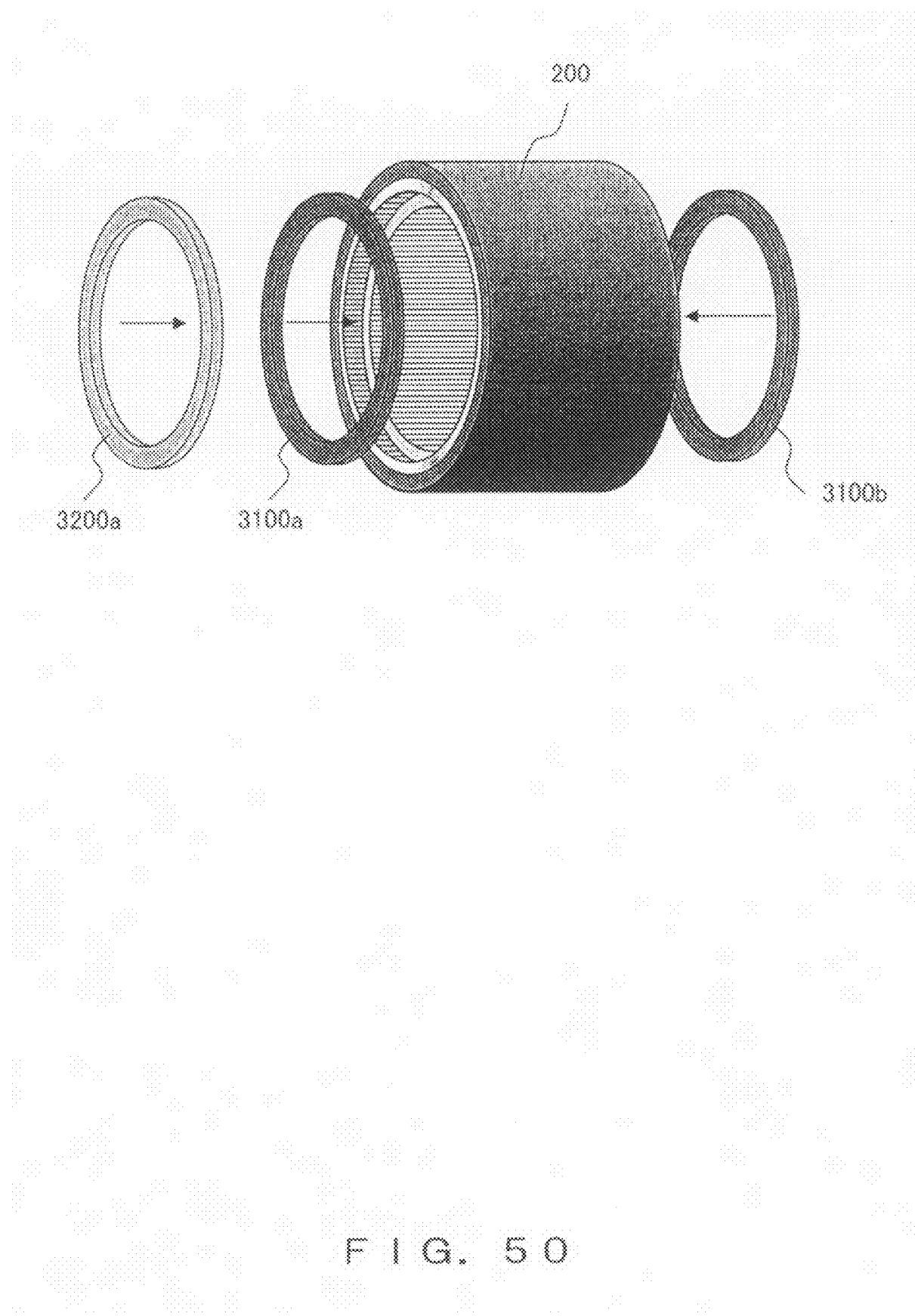
FIG. 50 is a diagram describing a comprisal of a radial type ultrasonic transducer using an insulative member made of a fiber-reinforced thermosetting PPE.
Figure 51:
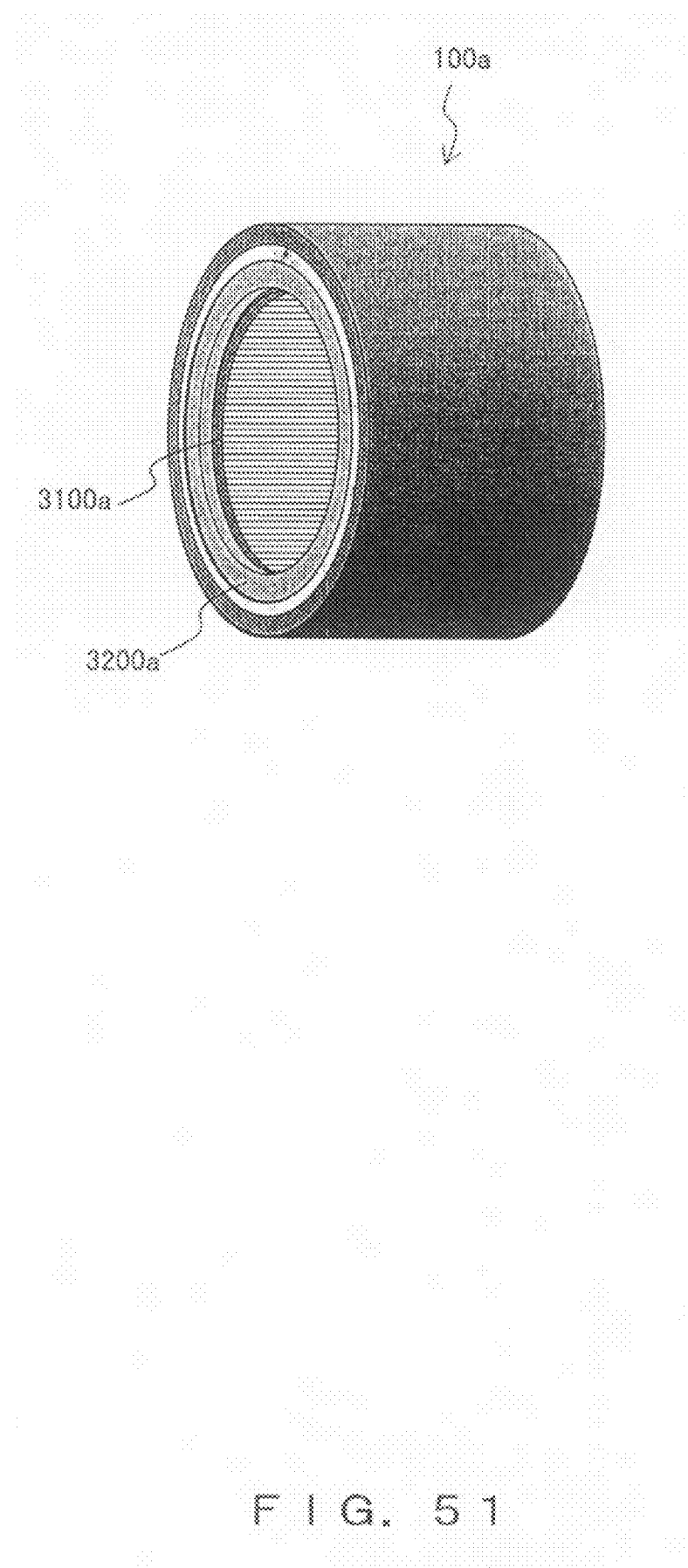
FIG. 51 is a diagram showing a radial type ultrasonic transducer using an insulative member made of a fiber-reinforced thermosetting PPE.

FIG. 50 is a diagram for describing a comprisal of a radial type ultrasonic transducer using an insulative member made of a fiber-reinforced thermosetting PPE, and FIG. 51 is a diagram showing a radial type ultrasonic transducer using an insulative member made of a fiber-reinforced thermosetting PPE.

In order to form a radial type ultrasonic transducer 100*a*, in the first step are prepared the acoustic matching layer 200, transducer shape forming members 3100*a* and 3100*b*, which are made of a hard material and formed into a cylindrical form in a prescribed size, and a cylindrically formed insulative member 3200*a*, which is made of a fiber-reinforced thermosetting PPE and formed into approximately the same shape as the transducer shape forming members 3100*a* and 3100*b*, as shown in FIG. 50.

Next, the transducer shape forming members 3100*a* and 3100*b* are fixed with a conductive adhesive integrally onto the acoustic matching layer 200, followed by the adhering of the insulative member 3200*a* to form the radial type ultrasonic transducer 100*a*, as shown in FIG. 51.

Figure 52:
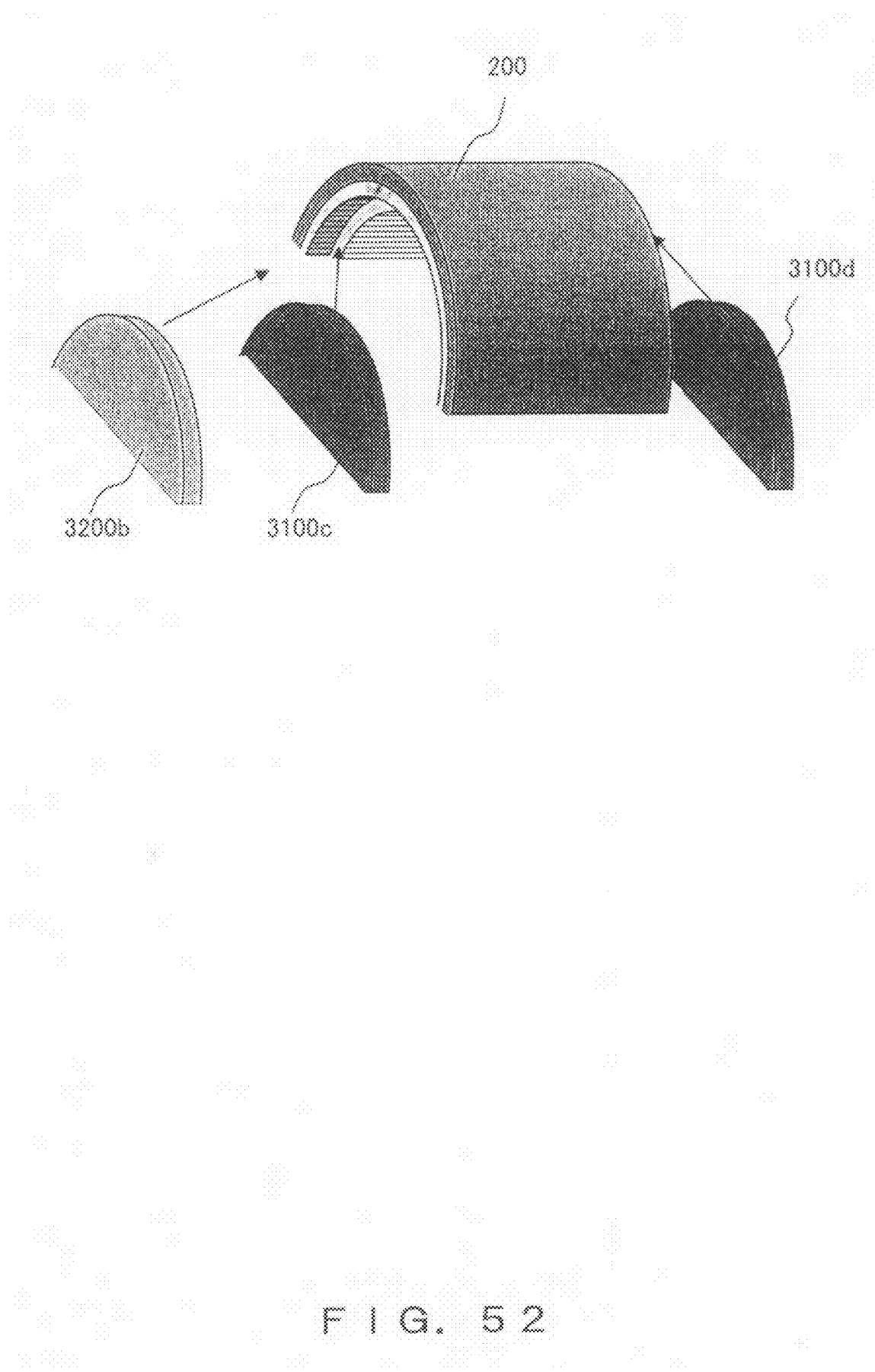
FIG. 52 is a diagram describing a comprisal of a convex type ultrasonic transducer using an insulative member made of a fiber-reinforced thermosetting PPE.
Figure 53:
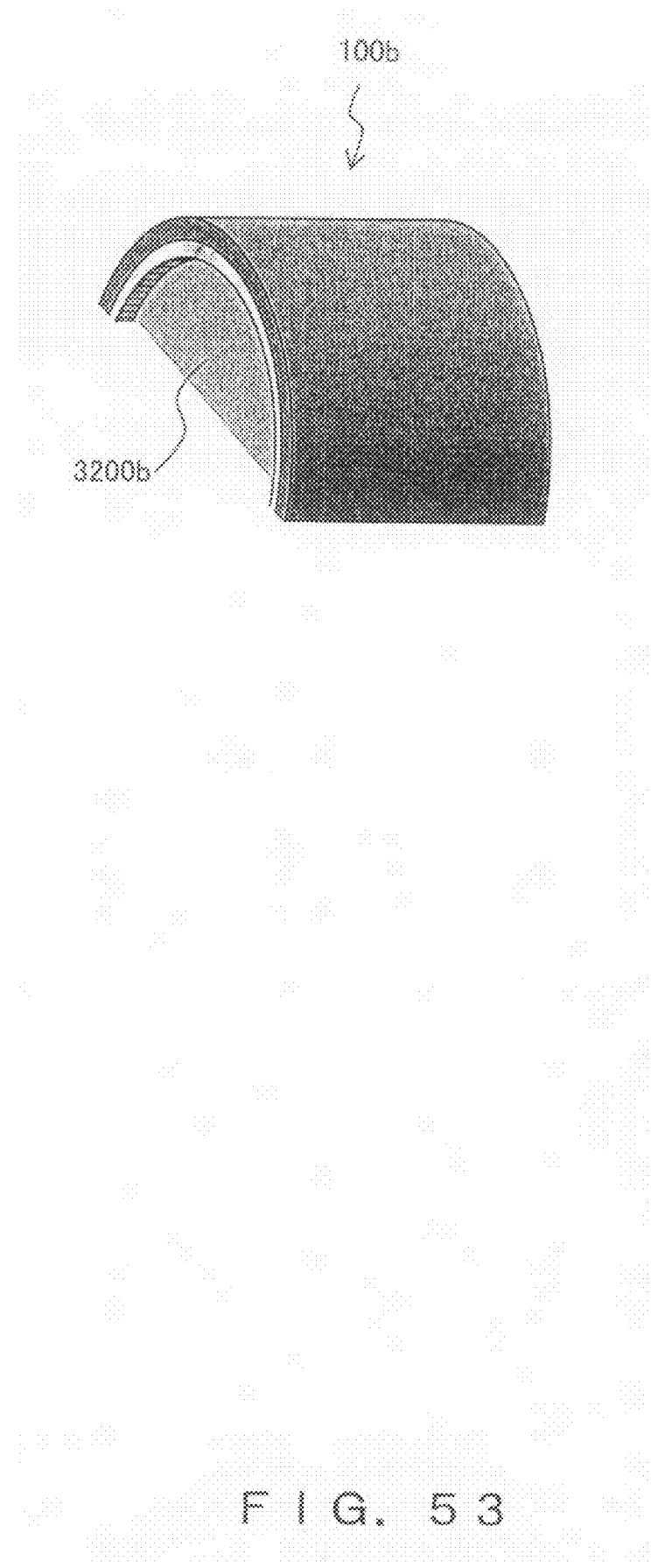
FIG. 53 is a diagram showing a convex type ultrasonic transducer using an insulative member made of a fiber-reinforced thermosetting PPE.

FIG. 52 is a diagram describing a comprisal of a convex type ultrasonic transducer using an insulative member made of a fiber-reinforced thermosetting PPE, and FIG. 53 is a diagram showing a convex type ultrasonic transducer using an insulative member made of a fiber-reinforced thermosetting PPE.

In order to form a convex type ultrasonic transducer 100*b*, in the first step are prepared the acoustic matching layer 200, transducer shape forming members 3100*c* and 3100*d*, which are made of a hard material and formed into a semi-disc shape of a prescribed size, and an insulative member 3200*b* that is made of a fiber-reinforced thermosetting PPE and formed into a semi-disc shape of the same size as the transducer shape forming members 3100*c* and 3100*d*, as shown in FIG. 52.

Next, the transducer shape forming members 3100*c* and 3100*d* are fixed with a conductive adhesive integrally onto the acoustic matching layer 200, followed by the adhering of the insulative member 3200*b* to form the convex type ultrasonic transducer 100*b*, as shown in FIG. 53

Note that the present invention can be changed in various ways within the scope thereof in lieu of being limited to the embodiments described above. For example, the present embodiment is configured to place the board 700 in parallel with the piezoelectric elements 500 and to connect both of them together electrically by way of a conductive member; however, the present invention is not limited to the above and it is possible to position a board at the inside of the backing member or on the side surface thereof, or to integrate the frame and board, or to connect the board to the piezoelectric element by way of a thin metallic wire, et cetera.

The preferred embodiments of the present invention have so far been described by referring to the accompanying drawings; the present invention, however, can be changed or modified for improvement in various possible ways within the scope thereof, and is not limited to the embodiments described above.

As described above, the present invention is capable of creating an environment related to all of the materials and intervals between the ultrasonic transducer elements, thereby making it possible to obtain a uniform image quality in all 360 degrees.

The present invention also differentiates the colors of division members placed adjacent to a predefined ultrasonic transducer from those of the other division members and therefore a predefined ultrasonic transducer can be easily identified by the differently colored division member. This contrivance enables the easy identification of a predefined ultrasonic transducer no matter what system of the ultrasonic transducer array is being used.

The present invention also makes it possible to provide a highly reliable ultrasonic transducer capable of obtaining a good ultrasonic wave image by arraying divided piezoelectric elements highly accurately; this reliability comes as a result of preventing occurrences of a failure due to a residual stress.

The invention claimed is:

1. An electronic radial type ultrasonic transducer arraying, at even intervals in a cylindrical shape, a plurality of ultrasonic transducer elements that transmit and receive an ultrasonic wave, and layering a plurality of acoustic matching layers, wherein
   a gap formed on the side face of the ultrasonic transducer element is filled with the same material as that of the outermost layer of the acoustic matching layer.

2. The electronic radial type ultrasonic transducer according to claim 1, wherein
   the gap is approximately the same interval as the one between the ultrasonic transducer elements.

3. The electronic radial type ultrasonic transducer according to claim 1, wherein
   a member constituted by the same material as that of the outermost layer of the acoustic matching layer is installed in the gap.

4. The electronic radial type ultrasonic transducer according to claim 3, wherein
   the gap is filled with the member together with an adhesive constituted by the same material as that of the outermost layer of the acoustic matching layer.

5. The electronic radial type ultrasonic transducer according to claim 3, wherein
   the member is installed in a gap part sandwiched by a pair of parts of the ultrasonic transducer elements that are not the ones transmitting and receiving the ultrasonic wave.

6. An ultrasound endoscope comprising an electronic radial type ultrasonic transducer according to any of claims 1 through 5.

* * * * *